US008459464B2

(12) United States Patent
Senftleber

(10) Patent No.: US 8,459,464 B2
(45) Date of Patent: Jun. 11, 2013

(54) APPARATUS AND METHOD FOR SEDIMENTATION FIELD-FLOW FRACTIONATION

(76) Inventor: Fred C. Senftleber, Jacksonville, FL (US)

( * ) Notice: Subject to any disclaimer, the term of this patent is extended or adjusted under 35 U.S.C. 154(b) by 249 days.

(21) Appl. No.: 13/051,528

(22) Filed: Mar. 18, 2011

(65) Prior Publication Data
US 2012/0234731 A1  Sep. 20, 2012

(51) Int. Cl.
B03C 1/30 (2006.01)

(52) U.S. Cl.
USPC .............. 209/39; 209/12.1; 209/155; 73/39; 494/18

(58) Field of Classification Search
USPC .......... 209/12.1, 39, 155; 73/23, 39; 494/18, 494/182
See application file for complete search history.

(56) References Cited

U.S. PATENT DOCUMENTS

| | | | |
|---|---|---|---|
| 3,449,938 A | | 6/1969 | Giddings |
| 3,523,610 A | | 8/1970 | Purcell et al. |
| 3,986,442 A | | 10/1976 | Khoja et al. |
| 4,283,276 A | | 8/1981 | Grant |
| 4,425,112 A | * | 1/1984 | Ito .................................. 494/18 |
| 4,502,699 A | | 3/1985 | Mukerji |
| 4,737,268 A | * | 4/1988 | Giddings ..................... 209/12.2 |
| 6,136,171 A | * | 10/2000 | Frazier et al. ................. 204/450 |
| 6,171,865 B1 | * | 1/2001 | Weigl et al. ..................... 436/52 |
| 6,832,981 B2 | | 12/2004 | Witthaus et al. |
| 7,442,315 B2 | | 10/2008 | Cardot et al. |
| 2012/0234731 A1 | * | 9/2012 | Senftleber ....................... 209/39 |

OTHER PUBLICATIONS

J.C. Giddings, "Field-Flow Fractionation: Analysis of Macromolecular, Colloidal, and Particulate Materials," Science, 260, 1456 (1993).
X.-B. Wang, J. Vykoukal, F.F. Becker, and P.R.C. Gascoyne, "Separation of Polystyrene Microbeads Using Dielectrophoretic/Gravitational Field-Flow Frationation," Biophys. J., 7.
J.C. Giddings, F.J.F. Yang, M.N. Myers, "Sedimentation Field-Flow Fractionation," Anal. Chem., 46 1917 (1974).

* cited by examiner

Primary Examiner — Terrell Matthews

(57) ABSTRACT

Apparatuses and methods are described for the discrimination of particles using sedimentation field-flow fractionation operating without the use of rotating seals. Multiple lines of fluid and electrical communication are provided through a centrifugation unit comprising a fishhook-shaped umbilical conduit traveling from a stationary frame through a rotating guide frame to the separation channel. Twisting and tangling of the umbilical conduit enclosed communication lines are prevented by rotating the guide frame and separation channel in the same direction about an axis at an angular velocity ratio of 1:2. The design eliminates maintenance problems associated with rotating seals, simplifies channel installation and adjustment, and enables the use of multiple channels and the simultaneous application of multiple modes of field-flow fractionation either in concert or in a two-dimensional format. The design also enables the injector and/or detector to be mounted contiguously with the separation channel on the centrifugal rotor.

20 Claims, 20 Drawing Sheets

APPARATUS AND METHOD FOR SEDIMENTATION FIELD-FLOW FRACTIONATION

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This application relates generally to field-flow fractionation. More specifically, the application provides apparatuses and methods for the discrimination of particles using sedimentation field-flow fractionation operating without the use of rotating-seal type coupling devices.

2. Prior Art

Field-flow fractionation (FFF) is a single-phase elution-based particle separation and characterization technique developed in the late 1960's by J. C. Giddings at the University of Utah. The first patents for the technique were issued to John C. Giddings in Jun. 17, 1969 (U.S. Pat. No. 3,449,938) and to Edward M Purcell and Howard C. Berg in Aug. 11, 1970 (U.S. Pat. No. 3,523,610). To effect a separation using FFF, the sample particles to be discriminated are introduced into a fluid medium that is passing through a narrow enclosed channel typically formed from two closely spaced parallel or concentric surfaces. The thickness of the channel, defined by the distance between the surfaces, is typically in the range of 25 to 300 micrometers and is much smaller than the other two dimensions of the channel. As the fluid medium moves through the channel, its flow rate is adjusted to achieve laminar flow conditions producing a differential flow profile that is parabolic or near-parabolic in shape. The rate of fluid flow is greatest in the middle of the channel but decreases progressively as the surfaces are approached.

To discriminate the sample particles in the fluid medium, one or more fields or forces are applied across the narrow thickness of the channel, perpendicular to the fluid flow. As the fields or forces interact with the sample, particles having different characteristics or properties aggregate into different steady state equilibrium zones across the parabolic fluid profile. The exact mechanism involved in establishing the breadth and position of the zones in the fluid profile depends on (1) the characteristics and properties of the sample particles in the fluid medium, (2) the nature of the applied field or force, (3) the strength of the interactive coupling between particular sample particles and the applied field or force, and (4) the extent to which the particular sample particles experience opposing secondary and/or dispersive interactions or forces in the channel. Particles that aggregate into zones in the more rapidly moving fluid exit from the channel first. Other zones then follow depending on their relative position in the flow profile. Because of the differential nature of the fluid flow, sample particles elute from the channel at different times, thus providing discrimination and separation.

Since the inception of FFF, applications have continued to grow in number encompassing such diverse areas as biomedical research, environmental studies, industrial colloids, natural and synthetic polymers, mining, and pharmaceuticals. Being an elution technique, FFF is readily adapted to fraction collection and online coupling to almost any liquid chromatographic or particle detection system. Sample particles can range in size from 0.001 to 100 micrometers with little restriction on their form or composition. The versatility of FFF comes from the ability to tailor the type and strength of the field or force to the specific properties of the particles to be separated. It was even recognized fairly early in the development of FFF (summarized in Giddings, 1993) that living cells could be separated without loss of viability or functionality.

Of particular interest in the present work is sedimentation field-flow fractionation (SdFFF). In this mode, the force applied across the channel is sedimentary in nature and generated by rotating the channel around an axis at an appropriate speed. Because of the way the force is created, SdFFF is also sometimes called centrifugal field-flow fractionation. To avoid confusion, it should be pointed out that SdFFF as defined above is distinctly different from gravitational field-flow fractionation (GFFF) where the sedimentary force is due to gravity. The acceleration of gravity can be taken as a fixed value. In SdFFF, the force depends on the radial distance of the channel from the axis and the angular velocity of the rotation. The force can therefore be adjusted to a desired value or programmed to change with time and is independent of the orientation of the channel relative to the earth.

SdFFF is one of the more uniformly applicable modes of FFF and probably the most selective, being able to discriminate particles differing by as little as 5-10% in size. Particles are separated based on the universal properties of mass and volume. As most review articles about SdFFF point out (Giddings, 1993), however, the technique also has shortcomings, principal among them being the complexity of the instrumentation. Unlike in other modes of FFF where the channel is stationary and generally linear, in SdFFF the channel is curved and must be rotated about an axis to generate the required force. The difficulty generally arises in that a means must be provided to maintain fluid communication between the rotating channel and stationary components within the instrument.

The present state of the art for SdFFF instrumentation is typified by the devices described in U.S. Pat. Nos. 4,283,276 and 7,442,315 where the sedimentation force is generated by attaching the channel to the rotor of a centrifuge. Fluid communication is made to the channel using rotating-seal type coupling devices (or more simply called rotating seals). Typically, to provide a continuous supply of fluid medium to produce the laminar flow required in the channel, fluid is pumped through narrow bore tubing from a reservoir of some type to the channel. The particles to be separated are added to the fluid using an injection device usually placed between the pump and the channel. After passing through the channel, the fluid is directed through additional tubing to a detection device that may be used to monitor and/or characterize the sample particles being separated. To keep the tubing from twisting and becoming tangled as the channel rotates, the rotating seals are used in connecting the tubing between the rotating channel and the stationary pump (or injection device) and detection device.

Although simple in concept, it is the rotating seals that create most of the problems and limitations in the use of SdFFF. The principal troubles come from leakage, contamination, and sample damage, particularly when the seal is operated at high rotational speeds. In its most basic form, the seal is constructed of two cylindrical members, one rotatable and the other non-rotatable, in face-to-face contact with a small diameter hole bored straight through the center of both members and the interface between. The hole aligns along the rotatable axis of the rotatable member. To minimize voids that can contribute a loss of sample separation resolution, the size of the hole is generally kept below 0.02 inches (0.5 mm).

Leakage, which is typically the greatest problem with rotating seals, is generally due to wear at the contact interface as the rotating members slide against one another. Additional leakage is also caused by misalignment and separation between the cylindrical members brought about by vibration as the members rotate. Heat due to friction can further exacerbate the wear and can ultimately limit the rotational speed at which the seal can be operated. Heat and shear forces at the interface can also damage fragile sample particles. In addition, debris from wear can restrict flow and contaminate fluid as it passes through the seal interface. Numerous efforts have been made in prior art to minimize the effects of these problems as illustrated by U.S. Pat. No. 4,502,699 and the other patents cited therein. Lubricants and cooling systems have been introduced to control friction and the heat that results. Tension springs, cushion mounts, and flexible connections have been incorporated into the designs to help diminish vibration as the seal rotates. Although effective to varying degrees, most of the improvements add complexity and additional cost to the seal design while still not totally eliminating the problems. The rotating seals remain high maintenance and are the weak link in the SdFFF apparatus.

Another difficulty created by the use of rotating seals is that the seals limit the number of rotating lines of communication that can be established with the SdFFF channel and thus severely restrict the ways the SdFFF apparatus can be configured and operated. Since rotating seals must be mounted along the axis of rotation for the channel, the single-bore rotating seal described above can provide the SdFFF apparatus with only two lines of fluid communication, one on either side of the channel. The use of such seals therefore precludes expansion of the SdFFF apparatus to more sophisticated higher-order techniques employing multiple inlet/outlet ports, multiple independent SdFFF channels and/or the use of multiple fields or forces where additional rotatable lines of communication to the channel would be required.

As evidenced by the absences of examples in the literature, even the use of a concentric double-bore rotating seal as described in U.S. Pat. No. 4,502,699 provides little improvement over the use of the single-bore models in the development of higher-order techniques in SdFFF. The use of a plurality of channels, for example, could save considerable operator time and effort by enabling multiple samples or calibration standards to be analyzed or "screened" simultaneously under a variety of experimental conditions. This is particularly relevant in clinical and commercial applications where throughput is often an important factor. These capabilities could even be further expanded by using multiple fields and ports to provide greater resolution through two-dimensional operation and more selective particle isolation.

The rotating-seal type coupling devices currently employed in SdFFF are a major source of problems in both reliability and maintenance. In addition, the seals dramatically limit the ability to expand the instrumentation to permit more advanced, higher-order separation capabilities. It would therefore be of substantial interest and benefit to develop apparatuses with associated methodologies that would enable the SdFFF discrimination of sample particles without the use of rotating-seal type coupling devices to provide fluid communication to the SdFFF separation channel.

Accordingly, a need remains for an apparatus and method for sedimentation field-flow fractionation in order to overcome the above-noted shortcomings. The present invention satisfies such a need by providing an apparatus and method for sedimentation field-flow fractionation that is versatile in its applications, and overcomes one or more of the above-noted shortcomings.

BRIEF SUMMARY OF THE INVENTION

In view of the foregoing background, it is therefore an object of the present invention to provide apparatuses and methods for the discrimination of particles using sedimentation field-flow fractionation (SdFFF) operating without the use of rotating-seal type coupling devices (or more simply called rotating seals). Each embodiment of the apparatus comprises (1) a SdFFF channel assembly which forms the SdFFF channel where the actual discrimination and separation of particles takes place and (2) a centrifugation unit that rotates the SdFFF channel assembly to generate the necessary sedimentation forces. Each centrifugation unit incorporates a looping-tube, twist-compensating fluid transfer system, well known in the art of continuous-flow centrifugation, to enable fluid communication with the SdFFF separation channel. When connected to conventional liquid chromatographic devices such as pumps, injection devices, detectors, and fraction collectors, the present invention becomes a fully functional SdFFF system. All embodiments of the SdFFF apparatus described herein circumvent the reliability and maintenance problems that are associated with using rotating seals to provide fluid communication to and from the SdFFF separation channel. Many include features and capabilities that are difficult, if not impossible, to implement with apparatuses that depend on rotating seal technology.

Alternative embodiments of the present invention integrate means to create secondary forces that enable other modes of field-flow fractionation (FFF) to couple with the sedimentation forces to further enhance the selectivity of the apparatus to separate and isolate specific fractions of particles from complex sample mixtures. The secondary force can also be used to hold and concentrate the sample components at the entrance to the separation channel as part of what is called a "relaxation" procedure. This aggregates sample particles initially to a smaller volume in the slower moving fluid and can result in significantly greater separation resolution. In electrical field-flow fractionation (abbreviated as EFFF), for example, particles are exposed to an electrophoretic force that enables discrimination on the bases of size and charge. Other embodiments exploit the dielectrophoretic (DEP-FFF) and magnetic (MgFFF) properties of the particles to be separated. In some modes of FFF, the force is developed by imposing a gradient across the channel as in thermal (ThFFF) or concentration (CgFFF) field-flow fractionation or by directing a second independent flow stream across the channel as in flow (FlFFF) and asymmetric flow (AFFFF or AF4) field-flow fractionation. The secondary force can be oriented to align, oppose, or operate at some intermediate angle with respect to the sedimentation force. At an angle of 90°, the two fields create a two-dimensional distribution of sample particles. Additional fluid, electrical, optical, and mechanical communication means to produce and/or support the secondary force are provided using the looping-tube twist-compensating transfer system operating inside the centrifugation unit.

Other embodiments of the present invention employ a plurality of channels for parallel or serial analysis of sample particles. Channels may be arranged side-by-side, end-to-end, or stacked and may be designed to function independently or connected together sequentially or in an array to enable coupled operation. Many of the embodiments employ multiple inlets and/or outlets on the channels to accommodate the additional features and means for fluid communications. Embodiments incorporating a plurality of channels enable simultaneous analysis of multiple samples, enhanced precision through easy replication, and increased sample-loading capacity for preparative-scale separations, all while providing almost infinite flexibility in selecting and combining separation parameters.

In a non-limiting exemplary embodiment, an apparatus for sedimentation field-flow fractionation for the discrimination of particles in a fluid medium preferably includes a channel having an inlet port adapted to receive the fluid medium into the channel. Such a channel may have an outlet port adapted to pass the fluid medium out of the channel. The channel may have a width substantially greater than a thickness thereof which causes the fluid medium traveling through the channel to travel in a laminar flow fashion at different velocities according to a velocity profile across the thickness of the channel.

The apparatus may further include a stationary frame and an axis wherein the axis may be positioned at a predetermined location on the stationary frame. A mechanism for rotating the channel about the axis at a predetermined angular velocity is also provided, thereby creating a sedimentation force across a thickness of the channel normal to a direction of flow of the fluid medium through the channel. In this manner, the sedimentation force displaces the particles in the fluid medium to various positions across the velocity profile based on the strength of an interaction between the sedimentation force and the particles. An inlet tube may have a movable end and a stationary end wherein the movable end of the inlet tube may be connected to the inlet port and further rotatable about the axis coincidently with the channel. The stationary end of the inlet tube may be motionless and non-rotatably connected to the stationary frame.

The apparatus may further include an outlet tube having a movable end and a stationary end. Such a movable end of the outlet tube may be connected to the outlet port and further may be rotatable about the axis coincidently with the channel. The stationary end of the outlet tube may be motionless and non-rotatably connected to the stationary frame. A mechanism for configuring the inlet tube and the outlet tube is also provided to allow fluid communication between the movable and stationary ends of the inlet tube and between the movable and stationary ends of the outlet tube.

The present invention may further include a method for discriminating particles in a fluid medium using sedimentation field-flow fractionation. Such a method preferably includes the steps of: providing a channel having inlet and outlet ports as well as a width substantially greater than a thickness thereof; providing a stationary frame and an axis; positioning the axis at a predetermined location on the stationary frame; providing an inlet tube having a movable end and a stationary end; connecting the movable end of the inlet tube to the inlet port such that the movable end is rotatable about the axis coincidently with the channel; maintaining the stationary end of the inlet tube motionless; and non-rotatably connecting the stationary end of the inlet tube to the stationary frame.

The method may further include the steps of: providing an outlet tube having a movable end and a stationary end; connecting the movable end of the outlet tube to the outlet port such that the movable end is rotatable about the axis coincidently with the channel; maintaining the stationary end of the outlet tube motionless; non-rotatably connecting the stationary end of the outlet tube to the stationary frame; and configuring the inlet tube and the outlet tube to allow fluid communication between the movable and stationary ends of the inlet tube and between the movable and stationary ends of the outlet tube.

The method may further include the steps of: the inlet port receiving the fluid medium into the channel; rotating the channel about the axis at a predetermined angular velocity thereby creating a sedimentation force across a thickness of the channel normal to a direction of flow of the fluid medium through the channel; causing the fluid medium traveling through the channel to travel in a laminar flow fashion at different velocities according to a velocity profile across the thickness of the channel; the sedimentation force displacing the particles in the fluid medium to various positions across the velocity profile based on the strength of an interaction between the sedimentation force and the particles; and the outlet port passing the fluid medium out of the channel.

The embodiments and procedures included in the following descriptions of the present invention are given to illustrate the basic principles and versatility of the invention, and are not intended to limit the scope of the invention. Each embodiment was chosen to demonstrate a particular capability of SdFFF that can be performed without use of rotating seals to provide fluid communication with the SdFFF separation channel.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

Figure 1:
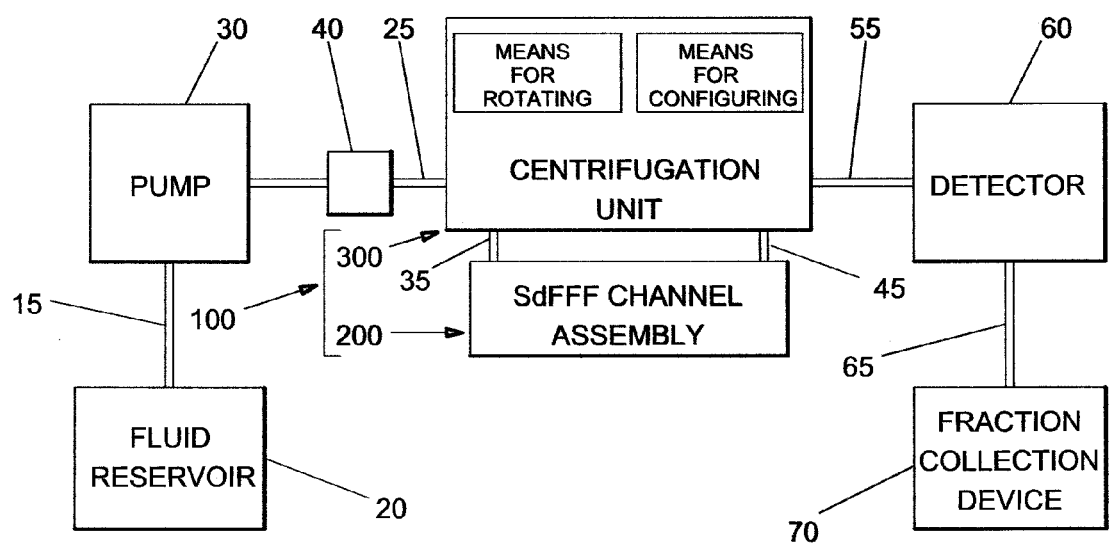
FIG. 1 shows a simplified schematic representation of one embodiment of a sedimentation field-flow fractionation system.

Those skilled in the art will appreciate that the figures are not intended to be drawn to any particular scale; nor are the figures intended to illustrate every embodiment of the invention. The invention is not limited to the exemplary embodiments depicted in the figures or the shapes, relative sizes or proportions shown in the figures.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "present invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The below disclosed subject matter is to be considered illustrative, and not restrictive, and the appended claims are intended to cover all such modifications, enhancements, and other embodiments which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

For clarity in presenting and understanding the present invention, the following definitions are provided. Unless defined otherwise, all technical and scientific terms used herein have the same meaning as is commonly understood by one of ordinary skill in the art to which this invention belongs. All patents, applications, and scientific publications cited in any section of this application are incorporated herein in their entirety. If a definition set forth in this section is contrary to or otherwise inconsistent with a definition set forth elsewhere in the patent or scientific literature incorporated by reference herein, the definition set forth in this section prevails.

The term "sedimentation field-flow fractionation" (abbreviated as SdFFF) as used herein shall refer to a mode of field-flow fractionation where the force applied across the separation channel is sedimentary in nature and generated by rotating a channel around an axis at an appropriate speed. The magnitude of the force depends on the radial distance of the channel from the axis and the angular velocity of the rotation. SdFFF is also sometimes called centrifugal field-flow fractionation. Although the sedimentation force is often expressed in units of gravity, 1 g=9.81 $m^2$/sec, the definition as used herein does not refer to a sedimentation force that is solely due to the acceleration of gravity. As sample particles are carried through the channel by a fluid medium, the sedimentary force interacts with and discriminates the particles causing particles having different characteristics or properties to aggregate into different steady state equilibrium zones across the thickness of the channel. Since the fluid medium exhibits a substantially parabolic flow profile as it moves through the channel, particles in faster moving fluid arrive at the end of the channel first followed sequentially by the slower particles, thus producing a separation of the particles in the sample.

The term "channel" or "separation channel" or "SdFFF channel" as used herein shall refer to an enclosed space or chamber having a thickness, a width, and a length of predetermined dimensions. The channel is formed between a top interior surface and a bottom interior surface, which are uniformly equidistant apart, and bordered by two ends and two sides. The thickness of the channel is the distance between the top and bottom interior surfaces and is substantially smaller than the width from side-to-side. The length is the expanse between the ends measured on a line midway between the top and bottom interior surfaces. The channel possesses at least one inlet port located towards one end for passing fluid medium into the channel and at least one outlet port located towards the other end for passing fluid medium out of the channel. The narrowness of the thickness causes the fluid medium traveling through the chamber to flow at different velocities according to a substantially parabolic velocity profile across the thickness of the channel.

The term "particle" or "sample particle" as used herein shall include materials less than about 100 micrometers in size whether rigid or deformable. The materials may be singular in nature or composed of aggregates or clusters, in any phase (solid, liquid, or gas) or combination thereof. The materials may be regular in shape or amorphous, natural occurring or synthetic. Although not limited to the following examples, this definition includes such materials as organic and inorganic macromolecules, polymers, and aggregates, nanotubes and related materials, emulsions and sols, micelles, dusts and powders, DNA, RNA, proteins, viruses, bacteria, plant and animal cells, cell aggregates, cell parts, and freshwater and marine organisms. Biological materials may be living or non-living. The materials may be dissolved, dispersed, suspended, or in any other form in the fluid medium.

The term "fluid medium" as used herein shall include any gas, liquid, supercritical fluid, or mixture thereof that may be used to dissolve, disperse, or suspend the sample particles. The fluid medium may be a pure substance or a mixture, inorganic or organic, polar or non-polar, an ionic liquid, or an aqueous solution. The medium may include dissolved materials to influence or control ionic strength, pH, surface tension, or other physicochemical characteristics. The fluid medium is used to carry the sample particles through the SdFFF apparatus and peripheral instrumentation and equipment (such as the pump, injection device, detector, and connecting tubing, and the like). The fluid medium has a velocity profile as it flows through the separation channel.

The term "velocity profile" as used herein shall refer to the variation of flow velocity of the fluid medium from point-topoint across the thickness of the separation channel. This variation is generally parabolic in shape as a consequence of laminar flow of the fluid medium through the channel. The shape of the profile, however, may be modified or produced artificially by intentionally introducing various flow streams of fluid medium into the channel at different flow velocities.

The term "equilibrium zone" as used herein shall refer to an area within the fluid medium where a population of particles with similar properties has aggregated. The position and breadth of the equilibrium zone across the thickness of the channel is governed by a balancing of opposing forces on the particles. Within the equilibrium zone, the net force on a particle is zero or almost zero. On one side is the interaction between the particles and the field or force (sedimentation, for example) applied across the thickness of the channel. On the opposing side are diffusion, steric effects, hydrodynamic lift forces, density gradients, and other transport and dispersion mechanisms. The migration of the equilibrium zone along the channel depends on the flow rate of the fluid medium at that particular position in its velocity profile.

The term "rotating seal" or "rotating-seal type coupling device" as used herein shall refer to any device used to transfer fluid (gas, liquid, or fluidized solid, or any combination thereof) or electrical signal between two or more substrates rotating at different velocities where the transfer is made across a moving or sliding interface. This includes slip-ring designs and devices where only one substrate is rotating.

The term "centrifugation unit" as used herein shall refer to a device that provides a mechanism for rotating and a mechanism for configuring for the present invention. The mechanism for rotating rotates the channel about an axis at a predetermined angular velocity creating a sedimentation force across the thickness of the chamber normal to the direction of flow of fluid medium through the channel. The created sedimentation force displaces sample particles in the fluid medium to various positions across a velocity profile based on the strength of an interaction between the sedimentation force and the particles. The mechanism for configuring configures, in combination, the movable and stationary ends of the inlet tube and outlet tube to allow fluid communication free of rotating seals between the movable and stationary ends of the inlet tube and between said movable and stationary ends of said outlet tube. The mechanism for configuring prevents twisting and tangling of the inlet and outlet tubes during rotation of said channel. In the arts, the centrifugation unit is also referred to as a continuous-flow centrifuge or a looping-tube twist-compensating centrifuge.

FIG. 1 shows a simplified schematic representation of one embodiment of an integrated field-flow fractionation system that employs the sedimentation field-flow fractionation (SdFFF) apparatus 100 disclosed in the present invention. For clarity, the SdFFF apparatus 100 is shown in this diagram as two parts: (1) the SdFFF channel assembly 200 which forms the SdFFF channel 250 (shown in FIG. 2) where the actual discrimination and separation of particles takes place and (2) the centrifugation unit 300 that rotates the SdFFF channel assembly 200 and provides fluid communication without the use of rotating seals between the SdFFF channel assembly 200 and the remainder of the system.

Centrifugation unit 300 provides a mechanism for rotating the channel 250 and a mechanism for configuring the inlet 35 and outlet 45 tubes. Fluid medium used in the separation process generally originates in a fluid reservoir 20. From the reservoir, the fluid is forced by pump 30 through the centrifugation unit 300 into the SdFFF channel assembly 200, then back to the centrifugation unit 300 and finally to the detector 60 and a fraction collection device 70, if collection is desired.

Sample particles to be separated may be added directly into the fluid reservoir 20 or introduced into the system using an injection device 40 placed typically in fluid communication line 25 between pump 30 and centrifugation unit 300. A six-port loop injector valve as commonly employed in liquid chromatography is suitable for this purpose, although other mechanism may work equally well.

In some alternative embodiments, the injection device 40 and detector 60 are incorporated into the centrifugation unit 300 in conjunction with inlet tube 35 and outlet tube 45, respectively. This configuration minimizes sample band spreading by reducing the length of tubing required to connect the injection device 40 and detector 60 to SdFFF channel assembly 200.

The pump 30 in the system may be of any design, but should be able to impel the fluid medium in a constant, unpulsating stream at flow rates of 0.01 to 10.0 milliliters/minute for analytical scale separations and appropriately higher for preparative scale work. Syringe, peristaltic, and well-damped reciprocating type pumps are typical. Flow rate control may be an integral part of the pump or a separate unit. To monitor or analyze the particles as they elute from the SdFFF channel assembly 200, one or more detectors are incorporated into the system. Detector 60 is often a conventional liquid chromatography or gel permeation chromatography detector, such as an ultraviolet/visible absorption detector or fluorescence detector.

More specific information about various particle parameters may be gleaned, however, by using a device such as a multi-angle laser light scattering (MALS) detector or one designed to provide direct chemical analysis such as an inductively coupled plasma spectrometer coupled directly to a mass spectrometer (ICP-MS). The detector 60 is preferably interfaced with a personal computer (not shown) for subsequent data handling and analysis. The computer can also be used to automate the injection device 40 and fraction collection device 70, control the flow rate provided by the pump 30, and program the rotational speed of the centrifugation unit 300 to which the SdFFF channel assembly 200 is attached. Centrifugation unit 300 and SdFFF channel assembly 200 will be described in more detail below with additional figures.

Fluid communication line 15 between the fluid reservoir 20 and the pump 30 is typically made with PTFE (polytetrafluoroethylene) tubing. To minimize band spreading and loss of separation resolution once sample particles have been introduced into the system, low volume (e.g. 0.02 inch ID) PEEK (polyetheretherketone) or comparable inert tubing is generally used for all other interconnections. This includes fluid communication line 25 between pump 30 and centrifugation unit 300, inlet tube 35 and outlet tube 45 connecting centrifugation unit 300 to SdFFF channel assembly 200, fluid communication line 55 joining centrifugation unit 300 to detector 60, and fluid communication line 65 connecting detector 60 to fraction collection device 70. Stainless steel tubing can also be used except for inlet tube 35 and outlet tube 45 where flexibility is essential.

Figure 2:
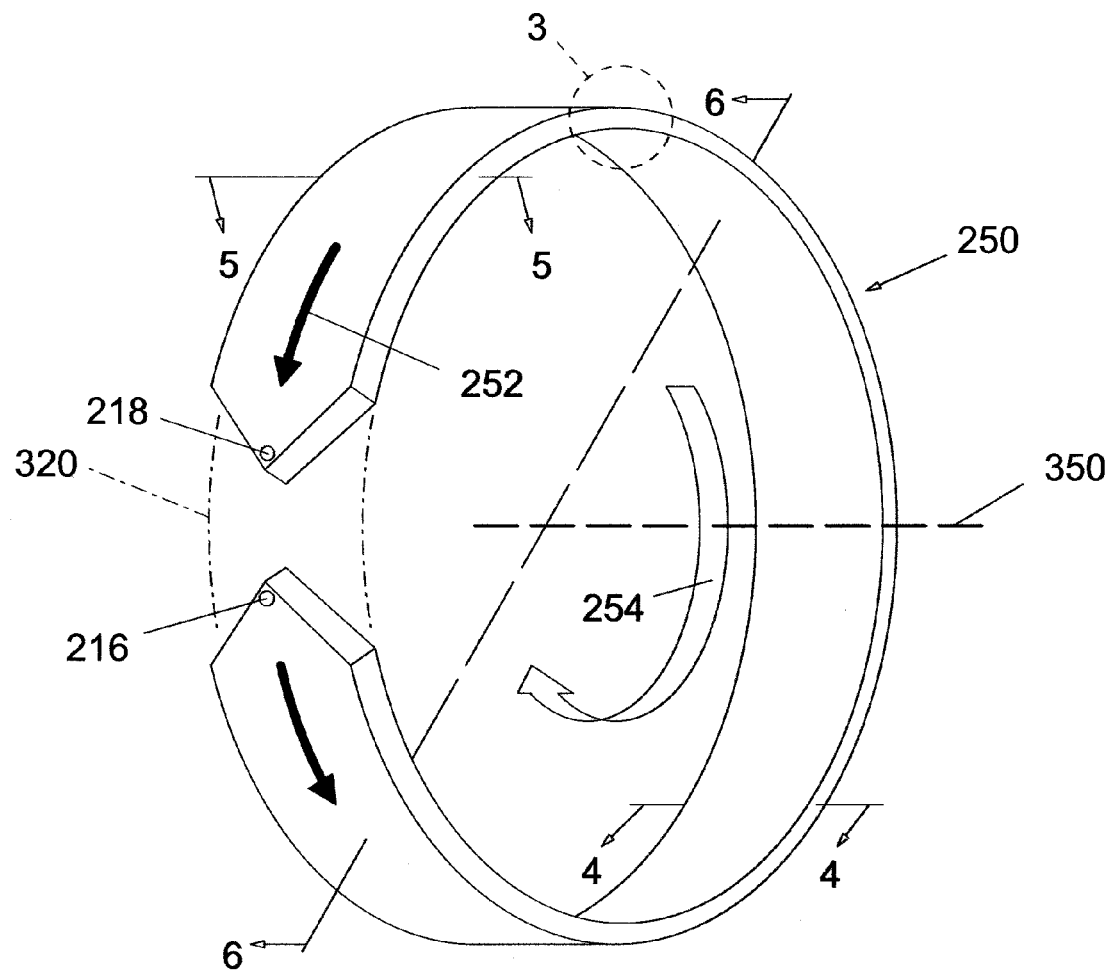
FIG. 2 shows a simplified isometric representation of a SdFFF channel according to one embodiment of the present invention.
Figure 3:
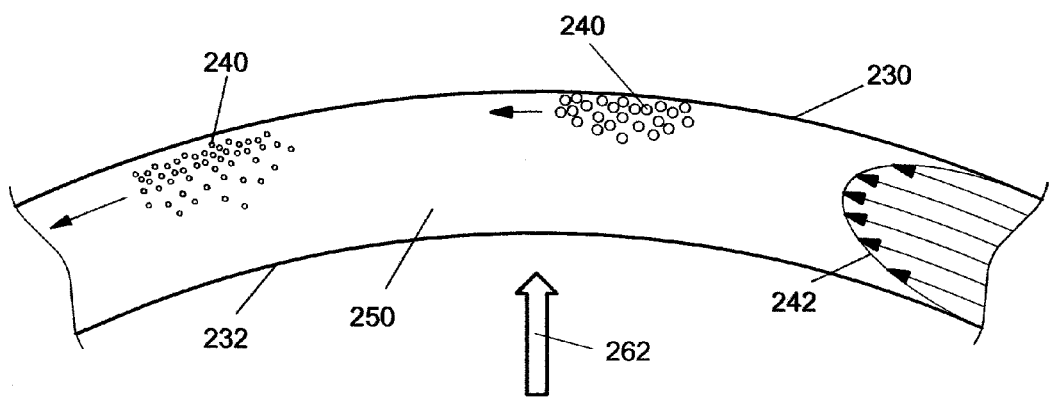
FIG. 3 shows a simplified schematic cross-sectional view perpendicular to fluid medium flow through part of a SdFFF channel as represented in FIG. 2.
Figure 4:
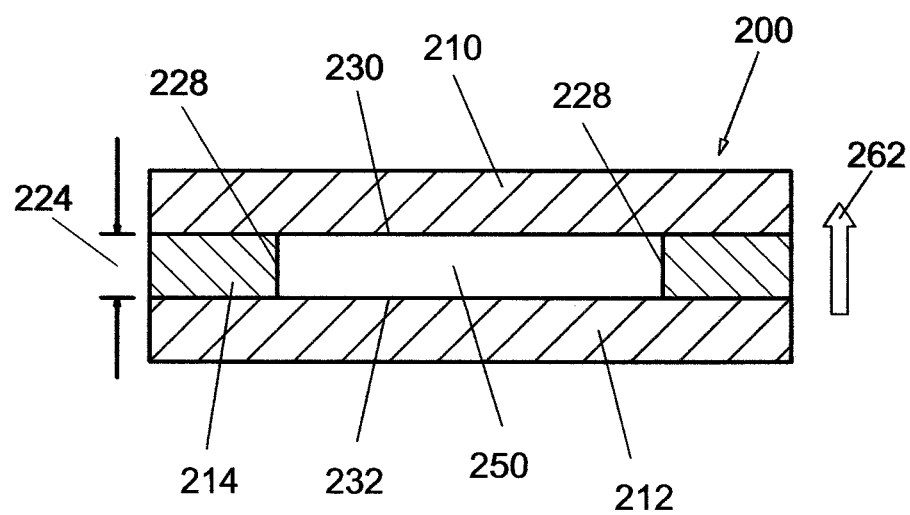
FIG. 4 shows a simplified schematic cross-sectional view of the SdFFF channel assembly in FIG. 2 from a perspective that is parallel to fluid medium flow through the SdFFF channel and perpendicular to the axis of rotation.
Figure 5:
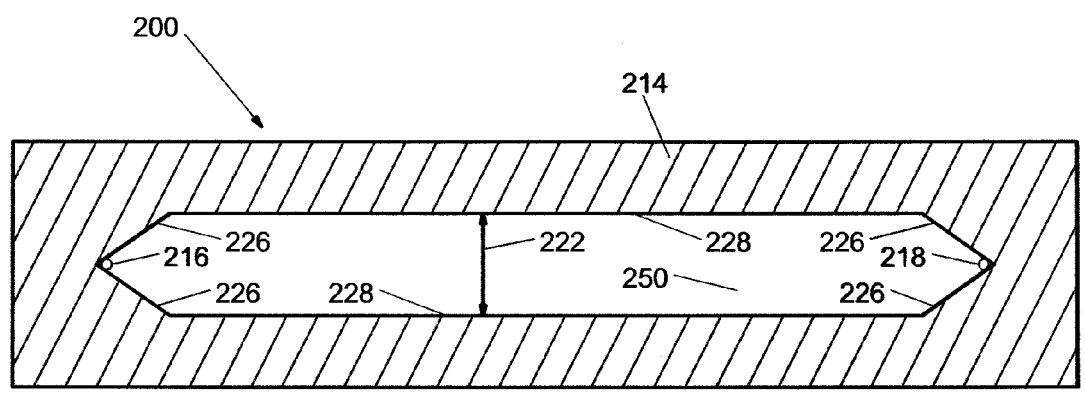
FIG. 5 shows a simplified schematic cross-sectional view of the SdFFF channel assembly in FIG. 2 from a perspective that is perpendicular to fluid medium flow through the SdFFF channel and radially perpendicular to the axis of rotation.
Figure 6:
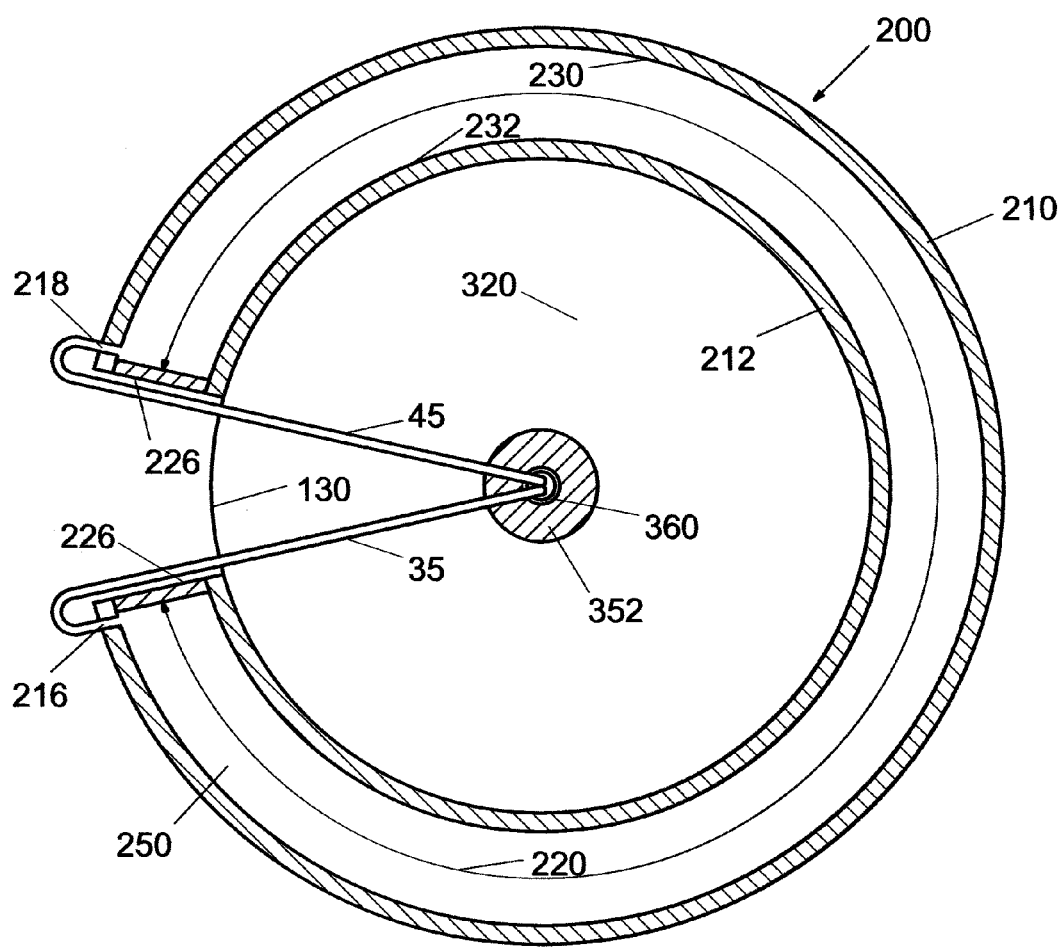
FIG. 6 shows a simplified schematic cross-sectional view of the SdFFF channel assembly in FIG. 2 from a perspective that is perpendicular to fluid medium flow through a SdFFF channel and parallel to the axis of rotation.

FIG. 2 shows a simplified isometric overview of a SdFFF channel 250 according to one embodiment of the present invention. The SdFFF channel 250 is actually the hollow cavity through which the fluid medium flows and only has shape as provided by the SdFFF channel assembly 200 and cylindrically shaped rotor 320 (dash-dot-dash lines) which are described in more detail in FIGS. 4-7. The sectional views of channel 250 shown in FIGS. 4-6 are designated in FIG. 2 by section lines 4-4, 5-5, and 6-6 and represent the sectional planes in the directions indicated. During typical operation of the SdFFF channel 250, fluid medium enters the inlet port 216, travels the length of the channel 250 and then exits through outlet tube 218. To minimize mixing in the SdFFF channel 250 due to the Coriolis effect, note that the direction of rotation 254 for the channel 250 around axis 350 is generally opposite the direction of flow 252 for the fluid medium. Additional description of the fluid medium is depicted in FIG. 3. The area represented in FIG. 3 is designated here by the dashed circular line labeled 3.

Figure 15A:
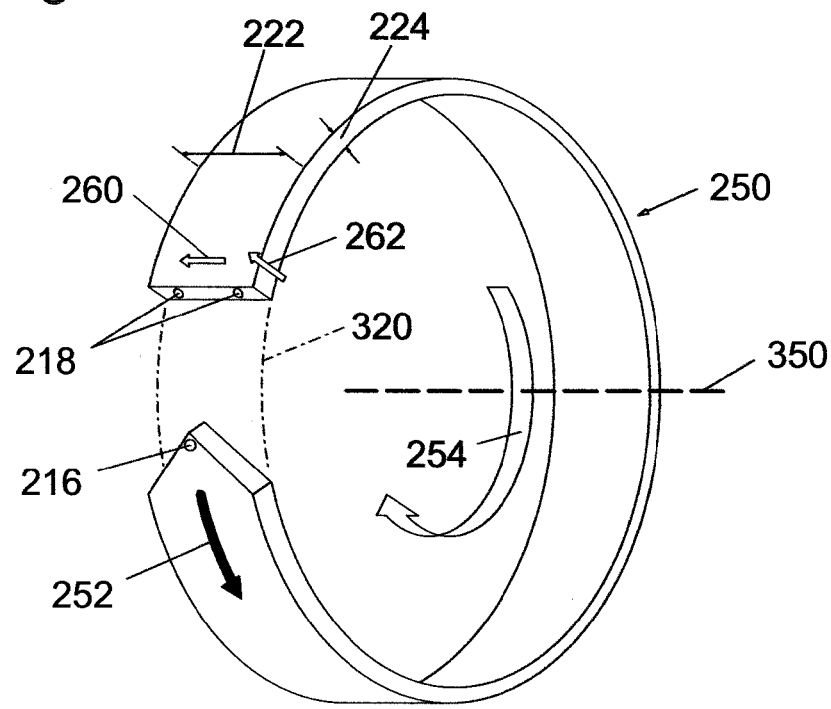
FIG. 15A shows a simplified isometric representation of one embodiment of a SdFFF channel which employs a two-dimensionally coupled secondary force and multiple outlet ports. The sedimentary force is across the thickness of the channel with the secondary force across the width.
Figure 15B:
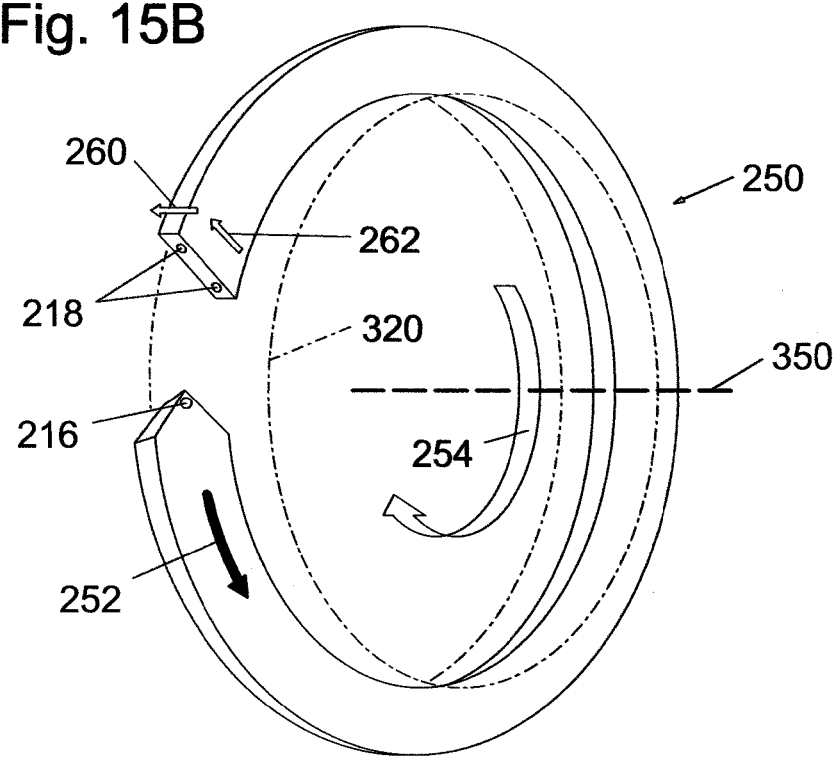
FIG. 15B shows a simplified isometric representation of one embodiment of a SdFFF channel which employs a two-dimensionally coupled secondary force and multiple outlet ports. The sedimentary force is across the width of the channel with the secondary force across the thickness.

FIG. 3 shows a simplified schematic cross-sectional view perpendicular to fluid medium flow through part of a SdFFF channel 250 as represented by the dashed circular line labeled 3 in FIG. 2. The SdFFF channel 250 is bordered by a top interior surface 230 and a bottom interior surface 232. The terms top and bottom are used here only to differentiate between the surfaces. The top interior surface 230 is always the surface that is more radially displaced from the axis 350 (shown in FIG. 2). As the SdFFF channel 250 rotates, a sedimentation force 262 is developed that interacts with the sample particles 240 in the fluid medium. Depending on several factors as discussed earlier, the particles 240 will aggregate into different steady state equilibrium zones. As the fluid medium flows through the channel 250, it does so in a laminar flow fashion and develops a parabolic or near parabolic flow velocity profile 242. A zone (particles 240 on the right of the diagram) in the more slowly moving flow streams in the velocity profile 242 near the top interior surface 230 travel more slowly through the SdFFF channel 250. A zone (particles 240 on the left) that is in more rapidly moving flow streams towards the center of the velocity profile 242 travel faster through the SdFFF channel 250. The discrimination of the particles 240 into zones by the sedimentation force 262 coupled with the different migration rates of the zones through the SdFFF channel 250 ultimately results in the separation of the particles 240. In FIGS. 15A and 15B, embodiments are shown that enable the velocity profile, and thus the migration of the particles, to be modified using multiple inlets on the channel 250.

FIG. 4 shows a simplified schematic cross-sectional representation of one embodiment of a SdFFF channel assembly 200 viewed from a perspective that is parallel to fluid medium flow through the SdFFF channel 250 and perpendicular to the axis 350 of rotation (shown in FIG. 2). This represents the sectional view from FIG. 2 taken at section line 4-4. The SdFFF channel assembly 200 comprises a first substrate 210 having a top interior surface 230 that is substantially smooth and both parallel to and concentric with the axis of rotation. First substrate 210 may be composed of a variety of solid materials including materials that are electrically and thermally conductive, semiconductive, or nonconductive in nature, and various composites or combinations thereof. First substrate 210 may also be composed of layers of the above materials or solid material covered or coated with liquid or semi-liquid materials.

SdFFF channel assembly 200 also comprises a second substrate 212 having a bottom interior surface 232 that is also substantially smooth and both parallel to and concentric with the axis of rotation. Second substrate 212 is separated from the first substrate 210 by a spacer 214. The distance between the top interior surface 230 and the bottom interior surface 232 defines the thickness 224 of the SdFFF channel 250 and is typically 25-500 micrometers, depending on the application. The spacer 214 also forms the two sides 228 of the SdFFF channel 250. As with the first substrate 210, the second substrate 212 and spacer 214 can be made of a variety of materials such as aluminum, copper, glass, polymer plastics, and the like, coated or uncoated. The spacer 214 may be a separate entity or may be formed by adding to or removing material from either the first substrate 210 or second substrate 212.

If a separate entity, a central portion of the spacer 214 material is removed to form the SdFFF channel 250. The second substrate 212 and spacer 214 may also be an integral part of the rotor 320 (shown in FIG. 2) to which the SdFFF channel assembly 200 is attached (see FIGS. 6 and 7). First substrate 210, second substrate 212, and spacer 214 may all be of the same material or different, but all must be chemically inert toward sample particles and the fluid medium and all must possess sufficient structural integrity to substantially maintain their shapes when exposed to the forces incurred during normal operation of the SdFFF apparatus 100.

Rotation of the SdFFF channel assembly 200 during normal operation produces a sedimentation force 262 across the SdFFF channel 250 in the direction indicated by the arrow. The method used to secure the parts of the channel assembly 200 to each other is highly dependent on the materials used in the construction. Common methods include the use of glue, or fasteners such as bolts, screws, or clasps, or the like. The SdFFF channel assembly 200 may be put together piece-by-piece directly on the rotor 320 or attached as a prefabricated entity. Disposable, short-term use channel assemblies 200 are particularly advantageous for clinical applications or where cross-contamination between samples or channel 250 clean-up is a particular problem.

FIG. 5 shows a simplified schematic cross-sectional view of the SdFFF channel assembly 200 from a perspective that is perpendicular to fluid medium flow through the SdFFF channel 250 and radially perpendicular to the axis 350 of rotation (shown in FIG. 2). This represents the sectional view from FIG. 2 taken at section line 5-5 or a horizontal cut through the spacer 214 and open central area of the SdFFF channel assembly 200 section shown in FIG. 4. For clarity, SdFFF channel assembly 200 is shown here as a flat entity, although in the apparatus 100 it is actually wrapped around the circumference of the rotor 320 (see FIGS. 6 and 7). The SdFFF channel 250 has two parallel sides 228, and an inlet port 216 and an outlet port 218 positioned at the vertices of two V-shaped ends 226. The distance between the sides 228 defines the width 222 of the SdFFF channel 250. Depending on the application, the width 222 (FIG. 5) may vary from 10 to 100 millimeters, with 20 millimeters being typical for analytical scale work. To minimize perturbations by the sides 228 of the SdFFF channel 250 on the velocity profile 242 (not shown) of the fluid medium, the width-to-thickness ratio for the channel 250 is normally kept on the order of 100 or larger.

The inlet port 216 and outlet port 218 shown in FIG. 5 (as well as in other embodiments) may take various forms in both size and shape. For example, the ports 216 and 218 may be round holes as small as several micrometers in width or elongated slots several centimeters in length. The periphery of the ports 216 and 218 may be designed or configured to extend to predetermined positions in the channel 250 to facilitate the deposition or removal of sample particles. Although FIG. 5 is a preferred embodiment, other acceptable embodiments may possess sides 228 that are not parallel, ends 226 that are not V-shaped, and/or a plurality of inlet ports 216 and/or outlet ports 218. Other configurations will be discussed below.

FIG. 6 shows a simplified schematic cross-sectional view of the SdFFF channel assembly 200 from a perspective that is perpendicular to fluid medium flow through a SdFFF channel 250 and parallel to the axis 350 of rotation (shown in FIG. 2). This represents the sectional view from FIG. 2 taken at section line 6-6. To highlight both the length 220 of the SdFFF channel 250 and the positions of the inlet port 216 and outlet port 218, FIG. 6 is not drawn to scale. The length 220 is defined here as the distance between the ends 226 of the SdFFF channel 250 as measured halfway between the top interior surface 230 on first substrate 210 and the bottom interior surface 232 on second substrate 212. The inlet port 216 and outlet port 218 are shown in FIG. 6 located near the ends 226 as openings in the top interior surface 230. Depending on the particular separation application, the ports 216 and 218 may also alternatively be located in the bottom interior surface 232, directly in the ends 226 of the channel 250, or any combination thereof.

The length 220 of the SdFFF channel 250 is typically 20-100 centimeters for conventional scale channels, but shorter for micro-size channels. When ports 216 and 218 are not located at the ends 226 of the channel 250, the effective length 220 is sometimes expressed as the distance between the ports 216 and 218. This corresponds to the distance traveled by sample particles during the separation process. In FIG. 6, the SdFFF channel assembly 200 is shown wrapped around and attached to the circumference of a cylindrically shaped rotor 320 in such a way that second substrate 212 is against the surface 130 of the rotor 320 and top interior surface 230 and the bottom interior surface 232 are concentric with the center of the rotor 320.

In an equally acceptable embodiment, SdFFF channel assembly 200 can be attached by way of the first substrate 210 to the inside wall or surface 130 of a round cake pan-shaped rotor 320 (not shown). The inlet tube 35 and outlet tube 45 are connected to inlet port 216 and outlet port 218, respectively, and provide fluid communication to the SdFFF channel 250. To facilitate removal or replacement of the SdFFF channel assembly 200 or the umbilical conduit 360, a disconnectable fitting (not shown) is generally included on tubes 35 and 45 at the point where the tubes enter the channel assembly 200. The tubes 35 and 45 are shown in FIG. 6 entering the umbilical conduit 360 at the center of the rotor 320. The umbilical conduit 360 is securely attached to the rotor 320 with the conduit fastener 352. In the embodiment depicted in FIG. 6, a single channel 250 is shown encompassing the entire circumference of the rotor 320. In other embodiments, a shorter channel 250 may be used or, as will be discussed in connection with FIGS. 16A/B and 17A/B, multiple channels 250 may be linked together.

In some embodiments, the injection device 40 and detector 60 (described in FIG. 1) are mounted directly on the rotor 320 and inserted into inlet tube 35 and outlet tube 45, respectively. This configuration minimizes sample band spreading by reducing the length of tubing required to connect the injection device 40 and detector 60 to the SdFFF channel 250. Any electrical communication device 276 and/or fluid communication device 278 required to operate the injection device 40 and detector 60 travel through the centrifugation unit 300 using the umbilical conduit 360 as described in more detail with FIGS. 7 and 8A/B. If the detector 60 is spectroscopic in nature, fiber optic cables can also be run through the same umbilical conduit 360.

Figure 7:
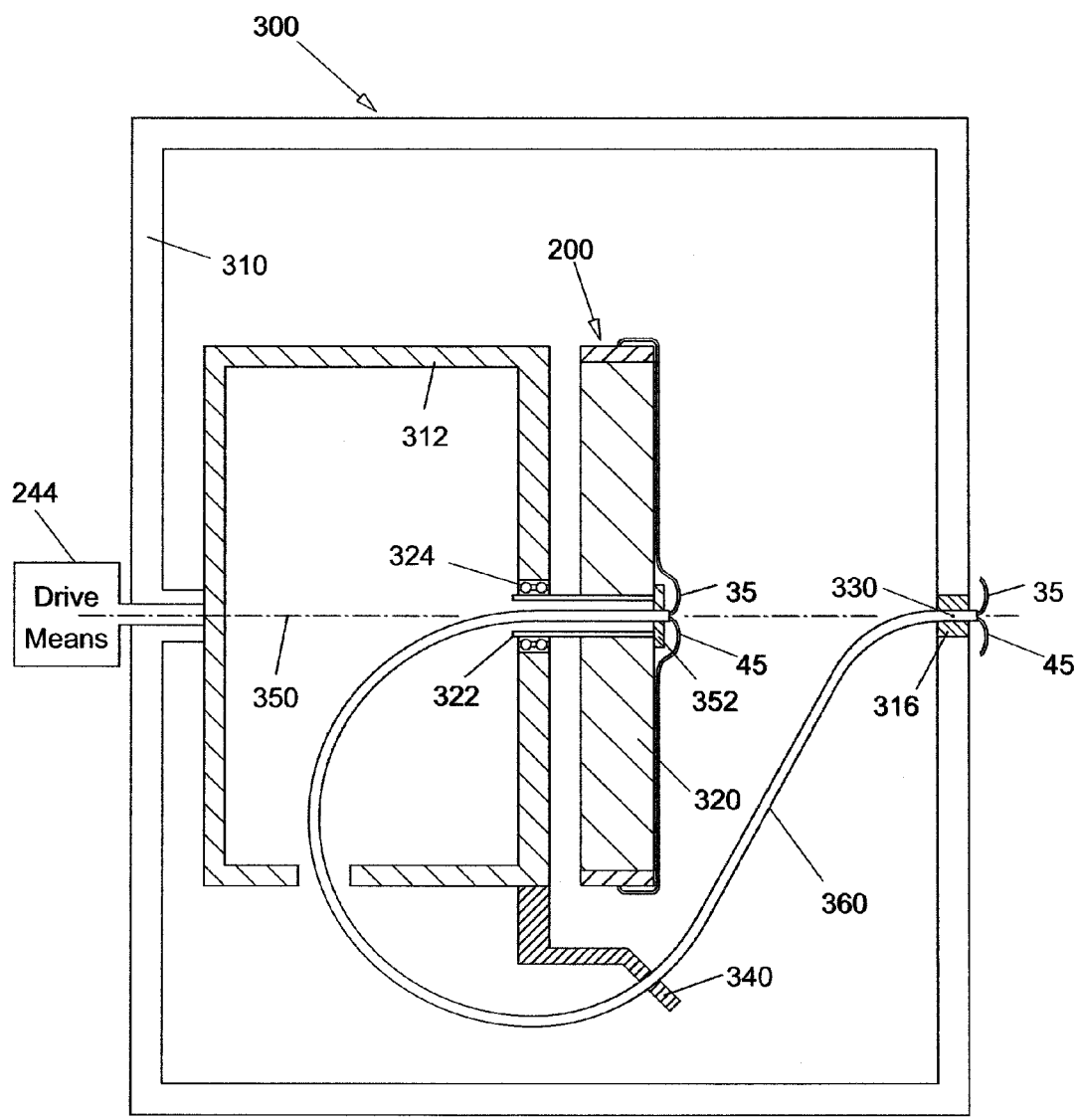
FIG. 7 shows one embodiment of a centrifugation unit that can be used to rotate the channel attached to the rotor while permitting samples and fluids to be transported and electrical connections made between the rotating channel and stationary support without using rotating seals or connections.

FIG. 7 shows a simplified schematic representation of one embodiment of a centrifugation unit 300 that can be employed as a way to enable fluid communication to the separation channel in a sedimentation field-flow fractionation apparatus without the use of rotating seals. As discussed in connection with FIG. 1, centrifugation unit 300 provides a mechanism for rotating the channel 250 (shown in FIG. 2) and a mechanism for configuring the inlet 35 and outlet 45 tubes. Centrifugation unit 300 is a continuous-flow centrifuge and operates in a fashion similar to the design described by Yoichiro Ito in U.S. Pat. No. 4,425,112.

The centrifugation unit 300 comprises a nested structure in which rotatable guide frame 312 is rotatably mounted inside a stationary frame 310 and is able to rotate about axis 350. Rotatable guide frame 312 is driven by a drive mechanism 244 at an angular velocity of R. The structural design and relative positions (nested versus not nested) of rotatable guide frame 312 and stationary frame 310 may vary as long as they are able to function as describe herein. A cylindrically-shaped rotor 320 is rotatably mounted to rotatable guide frame 312 using hollow shaft 322 and bearing 324. The axis of rotation for rotor 320 is coincidental with axis 350. Rotor 320 is driven by a drive mechanism 244 in the same direction of rotation as rotating guide frame 312 but at an angular velocity which is twice the angular velocity of rotating guide frame 312, or in other words, 2R. The drive mechanism 244 used to rotate the guide frame 312 and rotor 320 can be the same mechanism or different. Typically, a single mechanism is employed.

Correct synchronization and angular velocity ratio are assured by linking the rotation of the guide frame 312 and rotor 320 using gears, pulleys, magnetic and/or hydraulic coupling, and the like. The drive mechanism 244 is commonly a direct current (DC) permanent magnet motor that is regulated and monitored with a speed controller. The operational speed of the motor used for a particular separation application is generally expressed in revolutions per minute (rpm) and depends on the radial displacement of the channel 250 (shown in FIG. 2) within channel assembly 200 from the axis 350 of rotation and on the desired sedimentation force. Speed capabilities up to 2000 rpm suffice for most applications.

Centrifugation unit 300 is designed to enable inlet tube 35 and outlet tube 45 to travel from stationary point 330 on the stationary frame 310 to the inlet and outlet ports on SdFFF channel 250 without becoming twisted or tangled. To keep tubes 34 and 45 together along the looping fishhook-shaped path, the tubes are encapsulated in a flexible umbilical conduit 360. The stationary ends 334 of tubes 35 and 45 enter and are secured to umbilical conduit 360 at stationary tie-in unit 316 which is located along axis 350 and affixed to stationary frame 310 at stationary point 330.

Starting at stationary tie-in unit 316, flexible umbilical conduit 360 travels radially out around rotor 320 (crossing the rotor 320 from side-to-side) and through conduit guide member 340, an extended portion of rotating guide frame 312. Although shown in FIG. 7 as a separate part, conduit guide member 340 is actually considered to be part of rotating guide frame 312. An equally acceptable design incorporates the conduit guide member 340 into the rotating guide frame 312 directly as a single structure. The umbilical conduit 360 then continues looping through the side of rotating guide frame 312 and hollow shaft 322 until it reaches rotor 320 where the umbilical conduit 360 and tubes 34 and 45 are secured with conduit fastener 352. The entire centrifugal unit 300 should be structurally designed to ensure balance to prevent vibration when operated at high rotational speeds. The design should also make it easy to remove or replace the umbilical conduit 360 and rotor 320.

Although flexible umbilical conduit 360 is immobile at stationary tie-in unit 316, rotating at an angular velocity of R as it passes through conduit guide member 340, and at a angular velocity of 2R at the rotor, the conduit does not become twisted or tangled. The ability of this combined R/2R angular velocity ratio and fishhook-shaped configuration to prevent twisting in rotating systems is well known in the art of centrifugation and has been used commercially in blood apheresis equipment and elsewhere since the 1980s. Umbilical conduit 360 is generally made of flexible polymer tubing and is designed to protect the inlet tube 35 and outlet tube 45 as they pass through the centrifugation unit 300. Tubes 35 and 45 are depicted in FIG. 7 emerging from the umbilical conduit 360 at the center of rotor 320 and traveling across the face of the rotor 320. The movable ends 332 of tubes 35 and 45 are respectively connected to inlet 216 and outlet ports 218 on the channel 250 on the radially more distant side of the channel assembly 200. Alternatively, the tubes 35 and 45 may enter the channel assembly through the radially less distant side. The distinction will be discussed below in connection with relaxation techniques.

In the embodiment shown is FIG. 7, the SdFFF channel assembly 200 is wrapped around and attached to the circumference of rotor 320. The method of attachment depends on the design of the channel assembly 250 (see the discussion associated with FIGS. 4-6 and 9-17) and the integrity of the construction materials to withstand deformation under the influence of the sedimentation force. A convenient method is to use one or more standard or quick-release band clamps around the circumference of the channel assembly 200 and rotor 320. Alternatively glue, or fasteners such as bolts, screws, or clasps, or the like may be used. In other embodiments as discussed with FIG. 6, the SdFFF channel assembly 200 can be attached to the inside wall of a round cake pan-shaped rotor 320. With this design, a securing mechanism such as the system described by Cardot et al. (2008) in U.S. Pat. No. 7,442,315 works well.

Figure 8B:
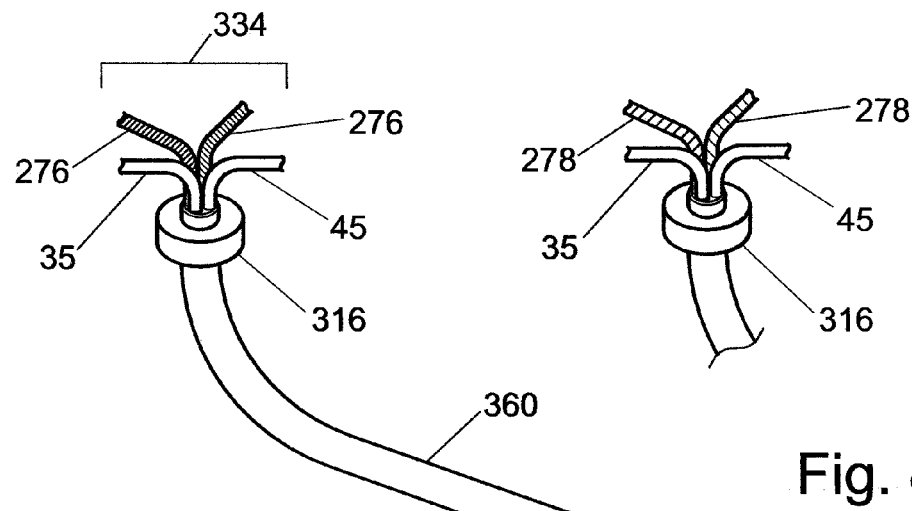
FIG. 8B shows a simplified schematic representation of one embodiment of the umbilical conduit enclosing four tubes.
Figure 8A:
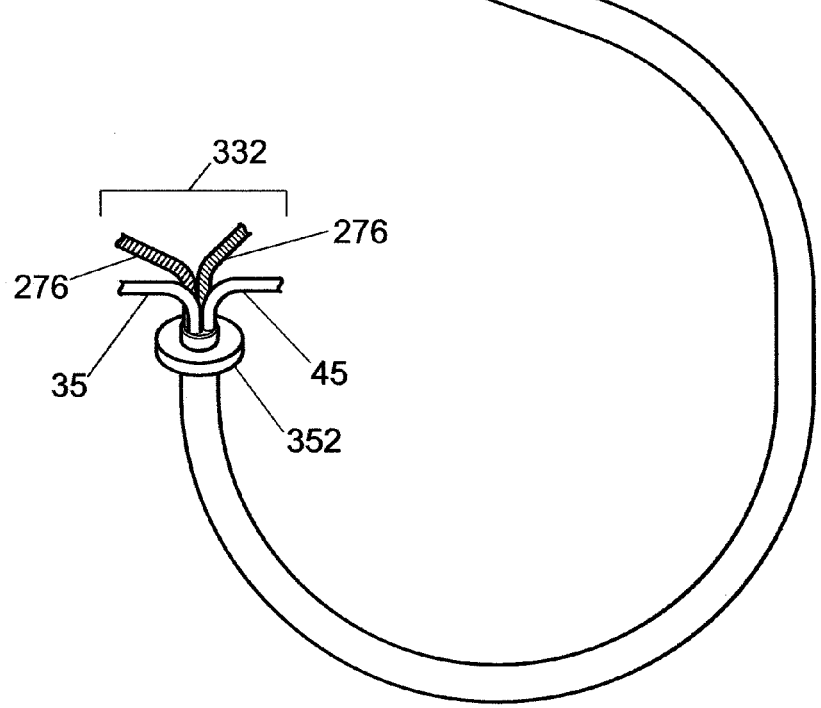
FIG. 8A shows a simplified schematic representation of one embodiment of an umbilical conduit enclosing two tubes and two electrical conductors.

FIG. 8A shows a simplified schematic representation of one embodiment of the umbilical conduit 360 enclosing the inlet tube 35, the outlet tube 45, and two electrical communication devices 276. One end of the umbilical conduit 360 is the stationary end 334 and is fastened to the stationary frame 310 (see FIG. 7) with the stationary tie-in unit 316 during typical operation. The other end of the umbilical conduit 360 is the movable end 332 and is secured to the rotatable rotor 320 (see FIG. 7) with conduit fastener 352. Tubes 35 and 45 provide fluid communication to the SdFFF channel assembly 200 that is attached to the rotor 320 (see FIG. 7).

FIG. 8A also shows two electrical communication devices 276. Although the electrical communication device 276 is typically copper wire, other types of conductors and materials may be used. The gauge or size of the conductor depends on the application. Electrical communication devices 276 are only included in the umbilical conduit 360 when electrical communication is needed on the rotor 320. The number of electrical communication devices 276 is not limited to two.

FIG. 8B also shows a simplified schematic representation of another embodiment of the umbilical conduit 360. In this representation, the umbilical conduit 360 includes two fluid communication devices 278 in addition to inlet tube 35 and outlet tube 45. The fluid communication device 278 is generally in the form of tubing that could be used to provide fluid communication with auxiliary devices or equipment needed on the rotor 320. The size, type, form, and material of the tubing depends on the application. Low volume PEEK, Teflon or other comparably flexible inert tubing works well for most applications. The number of fluid communication devices 276 is not limited to two. It should be pointed out that umbilical conduit 360 may also be used to carry other types of mechanism between the stationary tie-in unit 316 on the stationary frame 310 and the rotatable rotor 320 (FIG. 7). These other mechanism may include, but are not limited to: fiber optics, mechanical cables, and gas or pneumatic lines. To minimize mechanical strain and tension on the individual mechanism as the umbilical conduit 360 is rotated during normal operation of the centrifugal unit 300 (FIG. 7), the mechanism are preferably arranged within the umbilical conduit 360 using the guidelines described in U.S. Pat. No. 6,832,981.

In other embodiments of the SdFFF apparatus 100, additional components are added to the basic apparatus to enable the SdFFF technique to be coupled with other modes of field-flow fractionation. By coupling the techniques, additional parameters are introduced with which to discriminate the particles 240. The parameters enable the steady state equilibrium zones of aggregated particles 240 to be more highly focused and thereby provide higher resolution separations.

Figure 9:
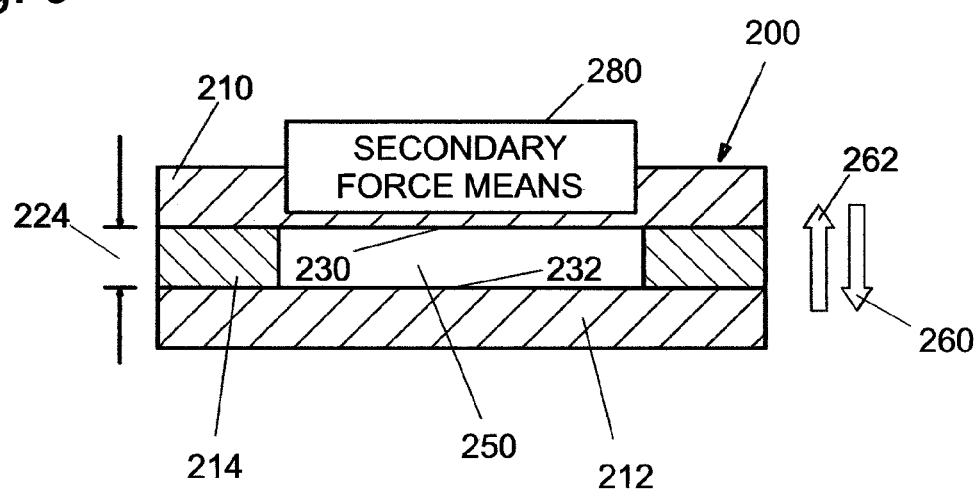
FIG. 9 shows a generalized schematic cross-sectional view of the SdFFF channel assembly as in FIG. 4 from a perspective that is parallel to fluid medium flow through a SdFFF channel and perpendicular to the axis of rotation. This view shows incorporated components enabling coupling of the SdFFF technique to other modes of field-flow fractionation.

FIG. 9 shows a generalized schematic cross-sectional view of the SdFFF channel assembly 200 that incorporates these additional components. The view is from a perspective that is parallel to fluid medium flow through the SdFFF channel 250 and perpendicular to the axis 350 of rotation, similar to the view shown in FIG. 4. In this embodiment, the SdFFF channel assembly 200 comprises a first substrate 210 having a top interior surface 230, spacer 214, and a second substrate 212 having a bottom interior surface 232 with the characteristics and composition as described above.

In addition, FIG. 9 shows a secondary force mechanism 280 for generating a secondary force 260 across the thickness 224 of the SdFFF channel 250. Typically the secondary force 260 is introduced in such a way that it opposes the sedimentation force 262 created by the rotation of SdFFF channel 250 around axis 350. In other analyses, however, it may be advantageous for the secondary force 260 and sedimentation force 262 to be aligned in the same direction. The secondary force 260 may be any force that interacts with the sample particles 240 (as shown in FIG. 3) and causes the particles 240 to move in a direction that is perpendicular to the flow of fluid medium through the SdFFF channel 250. The secondary force 260 may be applied simultaneously with the sedimentation force 262 or sequentially. The secondary force mechanism 280 is the mechanism by which the secondary force 260 is generated or developed.

Although shown in FIG. 9 inside the first substrate 210, the secondary force mechanism 280 may be inside the SdFFF channel assembly 200, outside, or both. In some modes, the secondary force 260 is developed by imposing a thermal or concentration gradient across the channel or by introducing a second independent flow stream to hydrodynamically influence the position of the particles 240. FIGS. 10-14E show several examples of secondary forces 260 and secondary force mechanism 280 that may be utilized. Understand that the present invention is not limited to just these examples. These were chosen to highlight how the present invention makes possible the coupling of a wide range of field-flow fractionation methodologies requiring only simple modifications to the SdFFF channel assembly. These coupled methodologies would be difficult to accomplish without the present invention.

Figure 10A:
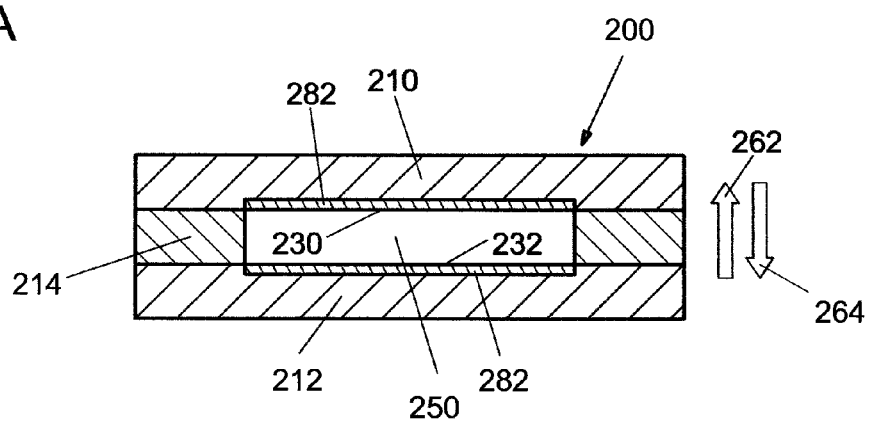
FIG. 10A, as in FIG. 9, shows a schematic cross-sectional view of the SdFFF channel assembly from a perspective that is parallel to fluid medium flow through a SdFFF channel and perpendicular to the axis of rotation. The embodiment shown in FIG. 10A incorporates components that enable the SdFFF technique to couple with electrical (or electrophoretic) field-flow fractionation (EFFF).

FIG. 10A shows a schematic cross-sectional view of the SdFFF channel assembly 200 that incorporates components that enable the SdFFF technique to be coupled with electrical (or electrophoretic) field-flow fractionation (EFFF). The view is from a perspective that is parallel to fluid medium flow through the SdFFF channel 250 and perpendicular to the axis 350 of rotation as in FIG. 9. This embodiment of the SdFFF channel assembly 200 includes two electrodes 282 that form the top interior surface 230 of the first substrate 210 and the bottom interior surface 232 of the second substrate 212. Substrates 210 and 212 themselves can function as the electrodes if conductive material is used. More commonly, the substrates 210 and 212 are fabricated from materials as described above and electrodes 282 with the desired characteristics are affixed, plated, sputtered, etched, or printed onto the surfaces.

Common photolithographic and electron-beam techniques may be used in constructing the electrodes 282, particularly when complex patterns are utilized. The electrode material should be highly electrically conductive and chemically inert to the sample particles 240 and fluid medium, and should generally possess high hydrogen over-potential when aqueous fluid mediums are used. Typical materials used to form the electrodes are carbon, gold, platinum, palladium, titanium, combinations and alloys thereof, and the like. The separation between the electrodes is determined by the spacer 214, constructed from non-conducting materials.

During operation, an electrical signal or potential difference of 0.5 to 3 volts is applied between the electrodes 282 to produce an electrical or electrophoretic force 264 across the channel 250. Preferably the voltage is kept below 1.7 volts to minimize electrolytic decomposition of the fluid medium. The electrical signal may be a direct current (DC) or an alternating current (AC) with a predetermined voltage, waveform, frequency, and phase or any combination thereof. The electrical signal may be applied continuously, intermittently, or programmed to change with time during the separation procedure. The electrical or electrophoretic force 264 developed from the electrical signal may be applied simultaneously with the sedimentation force 262 created by the rotation of SdFFF channel 250 around axis 350, or sequentially. The electrophoretic force 264 may be aligned substantially in the same direction as the sedimentation force 262 or in opposition to it.

Figure 10B:
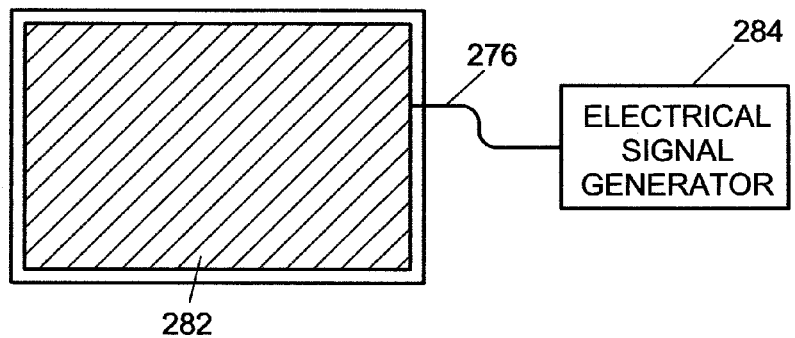
FIG. 10B shows an electrode that can be used in the SdFFF channel assembly in FIG. 10A.

FIG. 10B shows a surface view of an electrode 282 that may be used in the SdFFF channel assembly in FIG. 10A. In this embodiment, a single electrode covers the entire top interior surface 230 of the SdFFF channel 250, except in the triangular-shaped areas adjacent to the inlet 216 and outlet ports 218 (see FIG. 5). A similar electrode covers the bottom interior surface 232 of the SdFFF channel 250.

In other embodiments, both electrodes may be placed on either the top interior surface 230 or the bottom interior surface 232 or both electrodes may be placed on both the top interior surface 230 and the bottom interior surface 232. Each electrode 282 in connected to the electrical signal generator 284 by an electrical communication device 276. The electrical communication device 276 may pass from the stationary electrical signal generator 284 to the rotating SdFFF channel assembly 200 through the umbilical conduit 360 along with the inlet tube 35 and the outlet tube 45 (see FIG. 8A).

In additional embodiments, a plurality of electrodes 282 can be used, each covering a portion of the overall area of the aforementioned single electrode design. Each electrode 282 can be connected to the same or different electrical signal generator 284 with matching or dissimilar electrical signals. The electrical signals can be applied simultaneously or sequentially.

Figure 11A:
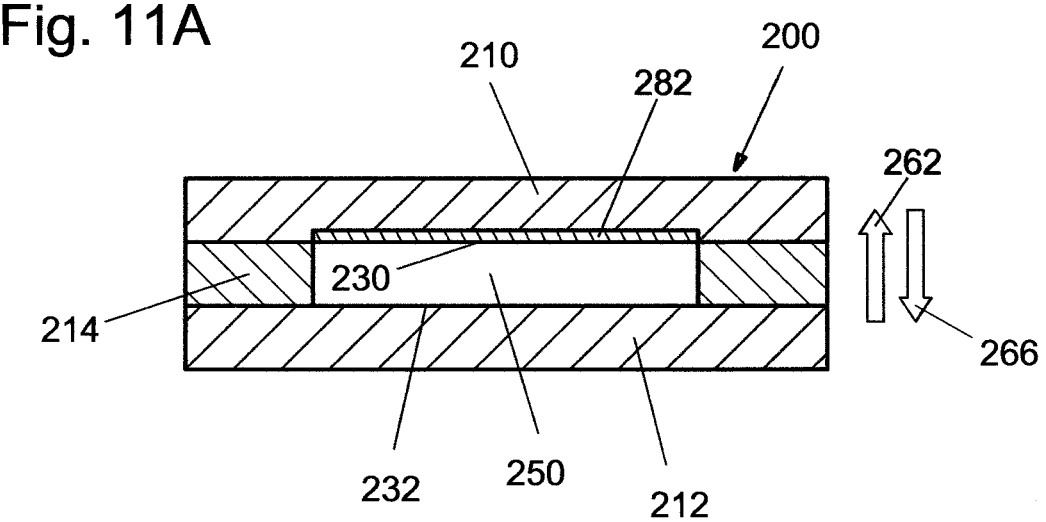
FIG. 11A, as in FIG. 9, shows a schematic cross-sectional view of the SdFFF channel assembly from a perspective that is parallel to fluid medium flow through a SdFFF channel and perpendicular to the axis of rotation. The embodiment shown in FIG. 11A incorporates components that enable the SdFFF technique to couple with dielectrophoretic field-flow fractionation (DEP-FFF).

FIG. 11A shows a schematic cross-sectional view of the SdFFF channel assembly 200 that incorporates components that enable the SdFFF technique to be coupled with dielectrophoretic field-flow fractionation (DEP-FFF). The view is from a perspective that is parallel to fluid medium flow through the SdFFF channel 250 and perpendicular to the axis 350 of rotation as in FIG. 9. This embodiment of the SdFFF channel assembly 200 includes two electrodes 282 (only one shown) that form the top interior surface 230 of the first substrate 210. There is no electrode on the bottom interior surface 232 of the second substrate 212.

In other embodiments, the electrodes 282 may be placed on both the top interior surface 230 and the bottom interior surface 232 or only on the bottom interior surface 232. The electrodes 282 may be in physical contact with the fluid medium or separated from it. The materials used to fabricated the substrates 210 and 212, the spacer 214, and electrodes 282 are similar that described above for FIG. 10A. To develop the dielectrophoretic force 266, an electrical signal is applied across the electrodes 282. This electrical signal may be a direct current (DC) or an alternating current (AC) with a predetermined voltage, waveform, frequency, and phase or any combination thereof. The electrical signal can be applied continuously, intermittently, or programmed to change with time during the separation procedure. The dielectrophoretic force 266 developed from the electrical signal can be applied simultaneously with the sedimentation force 262 created by the rotation of SdFFF channel 250 around axis 350, or sequentially. The dielectrophoretic force 266 can be aligned substantially in the same direction as the sedimentation force 262 or in opposition to it.

What differentiates DEP-FFF from EFFF is the way the developed forces interact with the sample particles. EFFF is typically applied to particles that possess a charge. Attraction between the particle and electrode is basically Coulombic in nature. Negative particles tend to migrate in solution toward the positive electrode. In aqueous solutions, a particle's charge can often be controlled by adjusting the pH of the solution. DEP-FFF is typically applied more to particles with an asymmetric charge distribution or to neutral polarizable particles into which an asymmetric charge distribution can be induced. For example, mammalian cells have been successfully discriminated and sorted using dielectrophoretic forces established in inhomogeneous AC electric fields (Wang, 1998). The strength of the interaction between the cell and force is highly dependent on the cell's composition and organization, features that reflect the cell's morphology and phenotype.

Figure 11B:
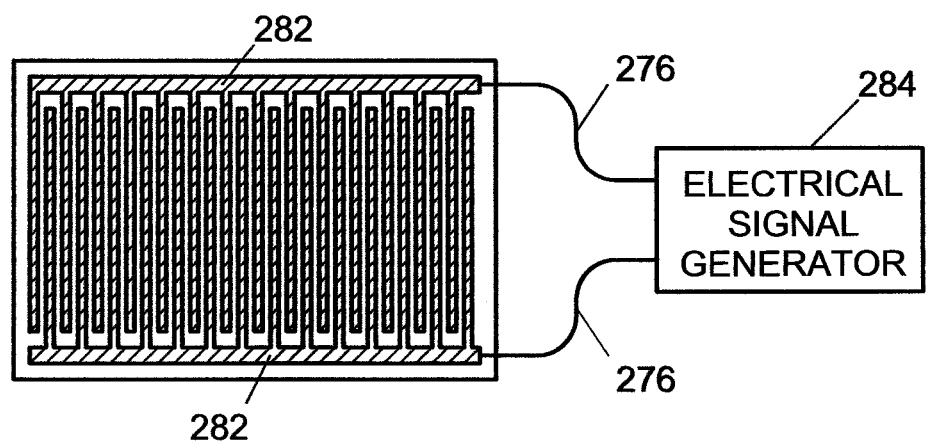
FIG. 11B shows a pair of electrodes that can be used in the SdFFF channel assembly in FIG. 11A.

FIG. 11B shows a surface view of a pair of interdigitated comb-shaped electrodes that can be used in the SdFFF channel assembly in FIG. 11A. In this preferred embodiment, the individual electrode elements are straight and evenly spaced. Other configurations, spacings, and shapes in which elements are curved, triangulated, castellated, or the like also work and may be more desirable in specific applications. Typically the electrodes 282 are arranged to cover the entire top interior surface 230 of the SdFFF channel 250, except in the triangular-shaped areas adjacent to the inlet 216 and outlet ports 218 (see FIG. 5). The electrodes 282 may be arranged to align substantially with the direction of flow of the fluid medium through the SdFFF channel 250, perpendicular to it, or at an angle. Each electrode 282 is connected to the electrical signal generator 284 by an electrical communication device 276.

The electrical communication device 276 may pass from the stationary electrical signal generators 284 to the rotating SdFFF channel assembly 200 through the umbilical conduit 360 along with the inlet tube 35 and the outlet tube 45 (see FIG. 8A). In additional embodiments, a plurality or an array of electrodes 282 may be used, each covering a portion of the overall area of the aforementioned electrode design and arrangement. Each electrode 282 may be connected to the same or different electrical signal generators 284 with matching or dissimilar electrical signals. The electrical signals may be applied simultaneously or sequentially.

Figure 12:
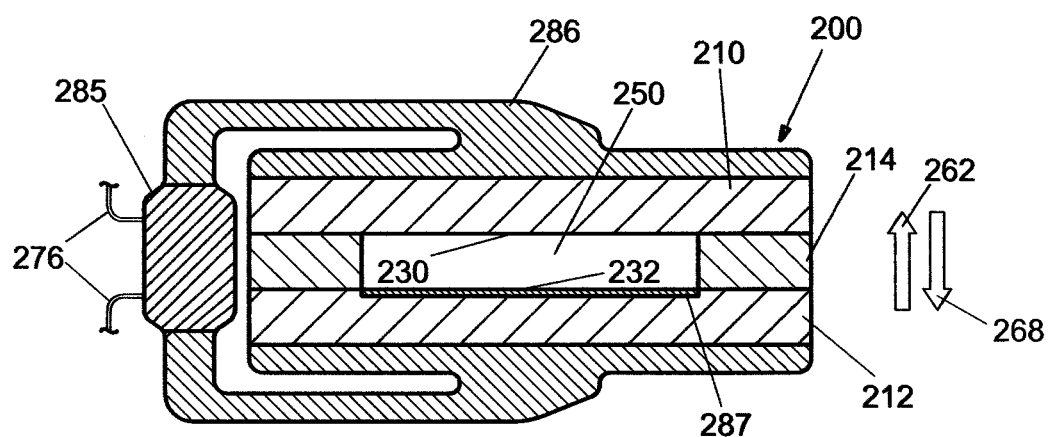
FIG. 12, as in FIG. 9, shows a schematic cross-sectional view of the SdFFF channel assembly from a perspective that is parallel to fluid medium flow through a SdFFF channel and perpendicular to the axis of rotation. The embodiment shown in FIG. 12 incorporates components that enable the SdFFF technique to couple with magnetic field-flow fractionation (MgFFF).

FIG. 12, as in FIG. 9, shows a schematic cross-sectional view of the SdFFF channel assembly 200 from a perspective that is parallel to fluid medium flow through a SdFFF channel 250 and perpendicular to the axis 350 of rotation. The embodiment shown in FIG. 12 incorporates components that enable the SdFFF technique to couple with magnetic field-flow fractionation (MgFFF). The SdFFF channel assembly 200 comprises a first substrate 210 having a top interior surface 230, spacer 214, and a second substrate 212 having a bottom interior surface 232 with the characteristics and composition as described above for FIG. 4.

Care must be taken in selecting materials for the fabrication, however, to insure that the materials have magnetic susceptibilities that accommodate the method used to produce the magnetic fields and forces employed in the MgFFF technique. It is the magnetic forces 268 that ultimately interact with the sample particles 240 and thus determine their position in the SdFFF channel 250. Several approaches may be used to generate the required forces 268. One method is to make the first 210 and second 212 substrates part of one or more magnets so that the magnet(s) actually form the top interior surface 230 and the bottom interior surface 232 of the channel 250.

A second more common approach is to situate a magnet 286 (or a plurality of magnets) just outside the channel 250 but in such a position that the magnetic field interacts directly with the sample particles 240 inside the channel 250. The magnet may be a permanent magnet or an electromagnet. Coil 285 is part of the electromagnet shown in FIG. 12. A third method, which is a variation on the second, is to use a magnet (or a plurality of magnets) outside the channel 250 to induce a magnetic field into a series of magnetically susceptible strips 287 positioned along or just behind the top interior surface 230 and/or the bottom interior surface 232 (only one strip shown). The magnetic field (or forces) 268 developed by the strips 287 then interacts with the sample particles 240.

As with the electrodes described in connection with FIGS. 11A and B, the shape, size, configuration, orientation, and number of strips depend on the specific application. A preferred embodiment of this third method uses long narrow strips placed parallel and evenly spaced, oriented perpendicular to the flow of the fluid medium through the SdFFF channel 250. A fourth approach is to make the strips 287 themselves a series of permanent or electromagnets 286 along or just behind the top interior surface 230 and/or the bottom interior surface 232.

An advantage of the strips 287 or individual magnets 286 is that the inhomogeneity of the magnetic field may be more easily controlled and exploited. The use of electromagnets as opposed to permanent magnets also enables the strength of the magnetic force 268 to be manipulated and the poles of the magnet 286 reversed. As with the systems described in FIGS. 10A/B and 11A/B, electrical power (or signal) for the electromagnets is provided by one or more electrical signal generators 284 by way of conductive electrical communication devices 276.

The electrical communication device 276 may pass from the stationary electrical signal generators 284 to the rotating SdFFF channel assembly 200 through the umbilical conduit 360 along with the inlet tube 35 and the outlet tube 45 (see FIG. 8A). Each strip 287 or electromagnet may be connected to the same or different electrical signal generators 284 with matching or dissimilar electrical signals. The electrical signals may be applied simultaneously or sequentially. The electrical signals may be a direct current (DC) or an alternating current (AC) with a predetermined voltage, waveform, frequency, and phase or any combination thereof. The electrical signals may be applied continuously, intermittently, or programmed to change with time during the separation procedure. The magnetic force 268 developed from the electrical signal may be applied simultaneously with the sedimentation force 262 created by the rotation of the SdFFF channel 250 around axis 350, or sequentially. The magnetic force 268 may be aligned substantially in the same direction as the sedimentation force 262 or in opposition to it.

Magnetic field-flow fractionation (MgFFF) is most applicable to sample particles that are permanently magnetic or materials with high magnetic susceptibility that can be induced to interact with a magnetic field. Many metals and metal complexes from both environmental and industrial sources fall into this category. Another broad area of potential application is in biomedical techniques utilizing magnetic labeling of cells. Very effective labeling methodologies have been developed to magnetically tag mammalian cells, even stem cells, using superparamagnetic iron oxide nanocomposites through adsorption and endosomal encapsulation processes that do not interfere with cell viability or proliferation.

Figure 13:
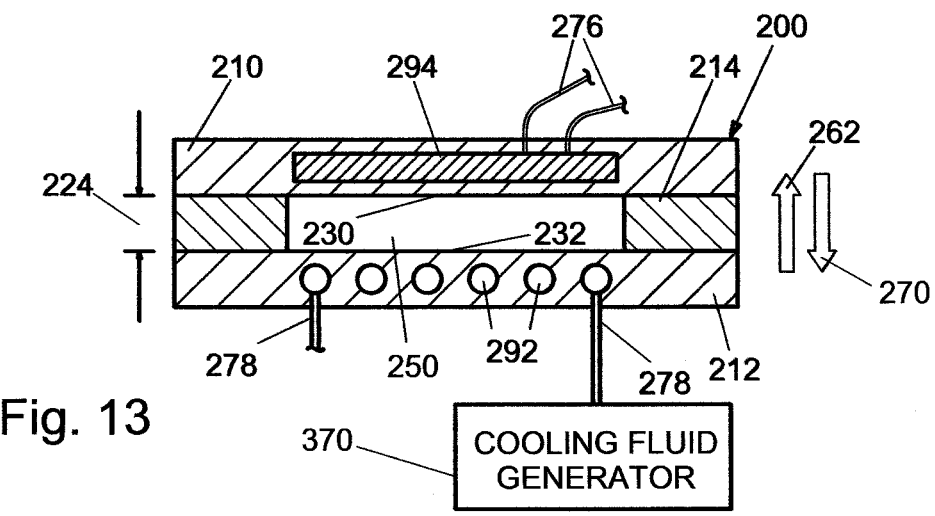
FIG. 13, as in FIG. 9, shows a schematic cross-sectional view of the SdFFF channel assembly from a perspective that is parallel to fluid medium flow through a SdFFF channel and perpendicular to the axis of rotation. The embodiment shown in FIG. 13 incorporates components that enable the SdFFF technique to couple with thermal field-flow fractionation (ThFFF).

FIG. 13 shows a schematic cross-sectional view of the SdFFF channel assembly 200 that incorporates components that enable the SdFFF technique to be coupled with thermal field-flow fractionation (ThFFF). The view is from a perspective that is parallel to fluid medium flow through the SdFFF channel 250 and perpendicular to the axis 350 of rotation as in FIG. 9. The ThFFF technique requires that a strong thermal gradient be developed and maintained across the thickness 224 of the channel 250. The first substrate 210 and second substrate 212 are generally highly polished bars of cooper or aluminum that have been plated with nickel or chromium metal or coated an inert polymer to produce a smooth nonreactive surface. Other materials, however, may be substituted for the above metals.

For most designs, it is advantageous for the substrates 210 and 212 to spread heat rapidly and evenly To produce the thermal gradient, a heating device 294, typically a series of electrical cartridge heaters, is imbedded in the first substrate 210 adjacent to the top interior surface 230. A cooling device 292 is imbedded in the second substrate 212 adjacent to the bottom interior surface 232. The two surfaces 230 and 232 are separated by a non-heat conducting spacer 214 which also defines the thickness 224 of the channel 250. Typically the cooling device 292 comprises a cooling fluid (often water) circulating from a cooling fluid generator (often a reservoir of water) 370 through holes transversing the length of the second substrate 212. The temperature differential is generally established across the channel 250 by adjusting the temperature of the heating device 294 while maintaining the temperature of the cooling device 292 constant. This differential may be maintained at one value or programmed to change with time. Control is typically preserved at a precision of $0.2°$ C. by cycling the heaters on and off using a temperature regulator or computer-controlled system. The temperatures are monitored using solid-state probes incorporated into the substrates 210 and 212. To prevent heat loss, the entire SdFFF channel assembly 200 is well insulated. The additional electrical communication devices 276 and fluid communication devices 278 needed to accommodate the ThFFF components on the rotating SdFFF channel assembly 200 are included in the umbilical conduit 360 along with the inlet tube 35 and the outlet tube 45 (see FIGS. 8A and 8B).

The thermophoretic force 270 developed as a result of the thermal gradient in the above system drives the sample particles toward the bottom interior surface 212, the colder wall. The sedimentation force 262 is in the opposite direction. To align the thermophoretic 270 and sedimentation 262 forces, the positions of the cooling device 292 and heating device 294 would be switched. The two forces 262 and 270 may be applied either simultaneously or sequentially.

In other embodiments of the SdFFF channel assembly 200 that include ThFFFF, the temperature differential between the top interior surface 230 and bottom interior surface 232 may be produced using thermoelectric or thermoacoustic devices, heat pumps, heat exchangers, or similar methods. In any embodiment, attention should be paid to the boiling point of the fluid medium. Thermal gradients as high as 10,000° C./cm are sometimes necessary. With low boiling point fluid mediums, a restrictor of some type may be necessary in the outlet tube 45 to increase pressure, and thus the medium's boiling point, in the channel 250.

Figure 14A:
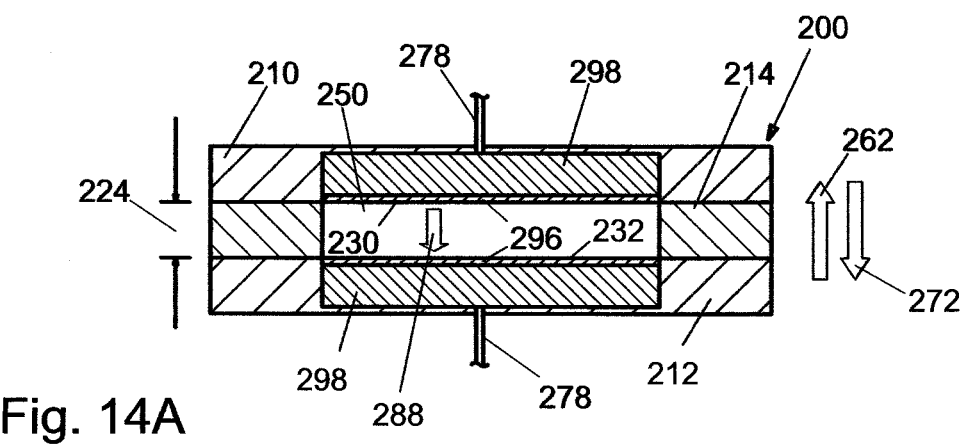
FIG. 14A, as in FIG. 9, shows a schematic cross-sectional view of the SdFFF channel assembly from a perspective that is parallel to fluid medium flow through a SdFFF channel and perpendicular to the axis of rotation. The embodiment shown in FIG. 14A incorporates components that enable the SdFFF technique to couple with symmetrical flow field-flow fractionation (FlFFF).

FIG. 14A shows a schematic cross-sectional view of the SdFFF channel assembly 200 that incorporates components that enable the SdFFF technique to be coupled with flow field-flow fractionation (FlFFF). The view is from a perspective that is parallel to fluid medium flow through the SdFFF channel 250 and perpendicular to the axis 350 of rotation as in FIG. 9. FlFFF differs from other modes of field-flow fractionation in that the force used to aggregate the particles originates from the movement of a displacement fluid 288 flowing across the thickness 224 of the channel 250 and perpendicular to the flow of the fluid medium.

In this embodiment, the top interior surface 230 and bottom interior surface 232 of the channel 250 are constructed of semi-permeable membranes 296 backed by support frits 298 to accommodate the flow of the displacement fluid 288. The preferred membrane 296 has a smooth flat surface, is non-compressible, enables a high flux, and exhibits a size exclusion (cutoff) that is significantly smaller than the sample particles. The membrane 296 should also be chemically inert and not adsorb the sample particles or other materials in the sample matrix. Regenerated cellulose, polysulfone, and polycarbonate ultrafiltration and microfiltration membranes 296, and the like, are commonly used with aqueous samples and fluid mediums.

For organic fluid mediums, polyamides and fluoropolymers are often used. The membranes 296 are affixed to support frits 298 that are typically constructed from polyethylene or polypropylene with 2-5 micrometer pore sizes. Ceramics or stainless steel may also be used for the support frits 298, although these materials are considerably more expensive and difficult to work with. The spacers 214 which define the thickness 224 of the channel 250, assuming no deformation of the membranes, are generally PTFE (polytetrafluoroethylene), boPet (biaxially-oriented polyethylene terephthalate), or polyimide.

The membranes 296 and support frits 298 comprise part of the respective first substrate 210 and second substrate 212. The remainder of substrates 210 and 212 form housings that encompass the support frits 298 and make the system liquid tight. When the fluid medium and displacement fluid 288 are aqueous, PMMA [poly(methyl methacrylate)] is convenient to use for this portion of substrates 210 and 212 because it readily allows visual inspection for air pockets that can impede the flow of displacement fluid 288 into the support frits 298. Other polymers or metals such as aluminum, copper or stainless steel may also be used.

The displacement fluid 288 is pumped to first substrate 210 by way of a fluid communication device 278, through the support frit 298 and membrane 296 that forms the top interior surface 230, across the thickness 224 of the channel 250, through the support frit 298 and membrane 296 that forms the bottom interior surface 232, and finally out of second substrate 212 by way of a second fluid communication device 278. The flow as described causes a hydrodynamic force 272 which can interact with sample particles in the channel 250 and opposes the sedimentation force 262 created by the rotation of the channel 250 around axis 350. If the flow of the displacement fluid 288 were reversed, the hydrodynamic force 272 and sedimentation force 262 would align. The hydrodynamic force 272 may be applied continuously, intermittently, or programmed to change with time during the separation procedure. Utilizing this embodiment, both SdFFF and FlFFF may be performed. The two forces 262 and 272 may be applied either simultaneously or sequentially.

Figure 14B:
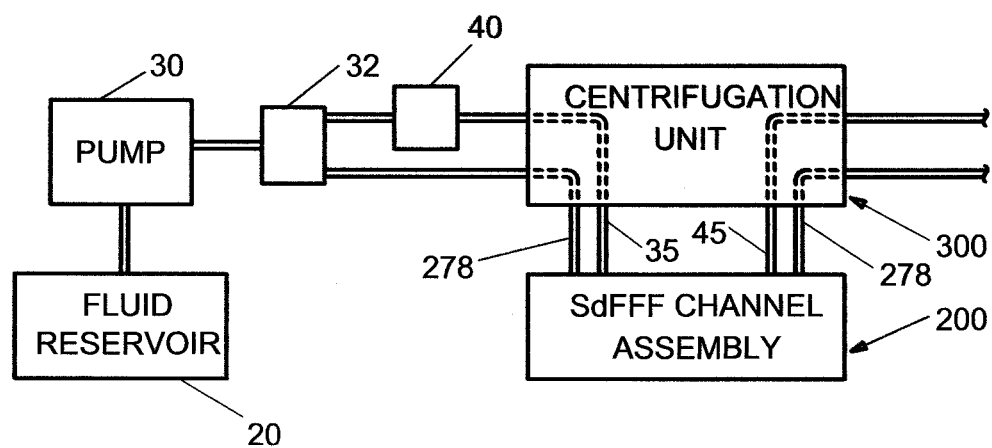
FIG. 14B shows a simplified schematic representation of one embodiment of a sedimentation field-flow fractionation (SdFFF) system that also enables symmetrical flow field-flow fractionation (FlFFF).

FIG. 14B shows a more general overview of one embodiment of a SdFFF/FlFFF system. Since the displacement fluid 288 (FIG. 14A) and fluid medium typically have the same composition, both may originate from the same fluid reservoir 20. Separate pumps may be used for the two fluid streams, each with its own flow controller 32. More commonly however, as shown in FIG. 14B, a single pump 20 is used and the stream is simply split. The flow controller 32 regulates both the overall flow and the proportion that becomes the fluid medium and the displacement fluid 288. After the stream split, the displacement fluid 288 flows through the fluid communication device 278 into centrifugation unit 300 and then continues to the SdFFF channel 250 (not shown) inside the SdFFF channel assembly 200. The fluid medium after the stream split passes through the sample injection device 40 before flowing through inlet tube 35 and into the centrifugation unit 300, the SdFFF channel assembly 200, and channel 250. The displacement fluid exits the SdFFF channel assembly 200 through a second fluid communication device 278. The fluid medium exits through the outlet tube 45. To keep the lines from becoming twisted and tangled, inlet 35 and outlet 45 tubes and the two fluid communication devices 278 all travel through the umbilical conduit 360 (see FIG. 8B) as they pass through the centrifugation unit 300.

Figure 14C:
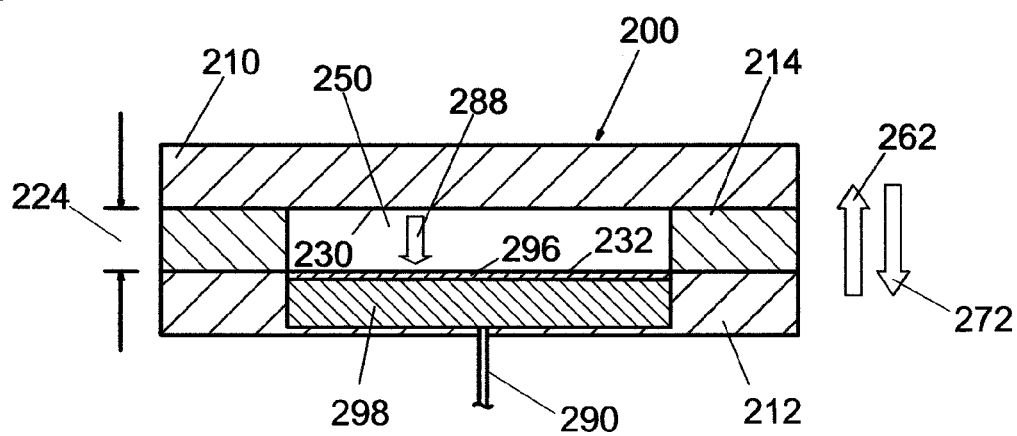
FIG. 14C, as in FIG. 9, shows a schematic cross-sectional view of the SdFFF channel assembly from a perspective that is parallel to fluid medium flow through a SdFFF channel and perpendicular to the axis of rotation. The embodiment shown in FIG. 14C incorporates components that enable the SdFFF technique to couple with asymmetrical flow field-flow fractionation (AFFFF or AF4).
Figure 14D:
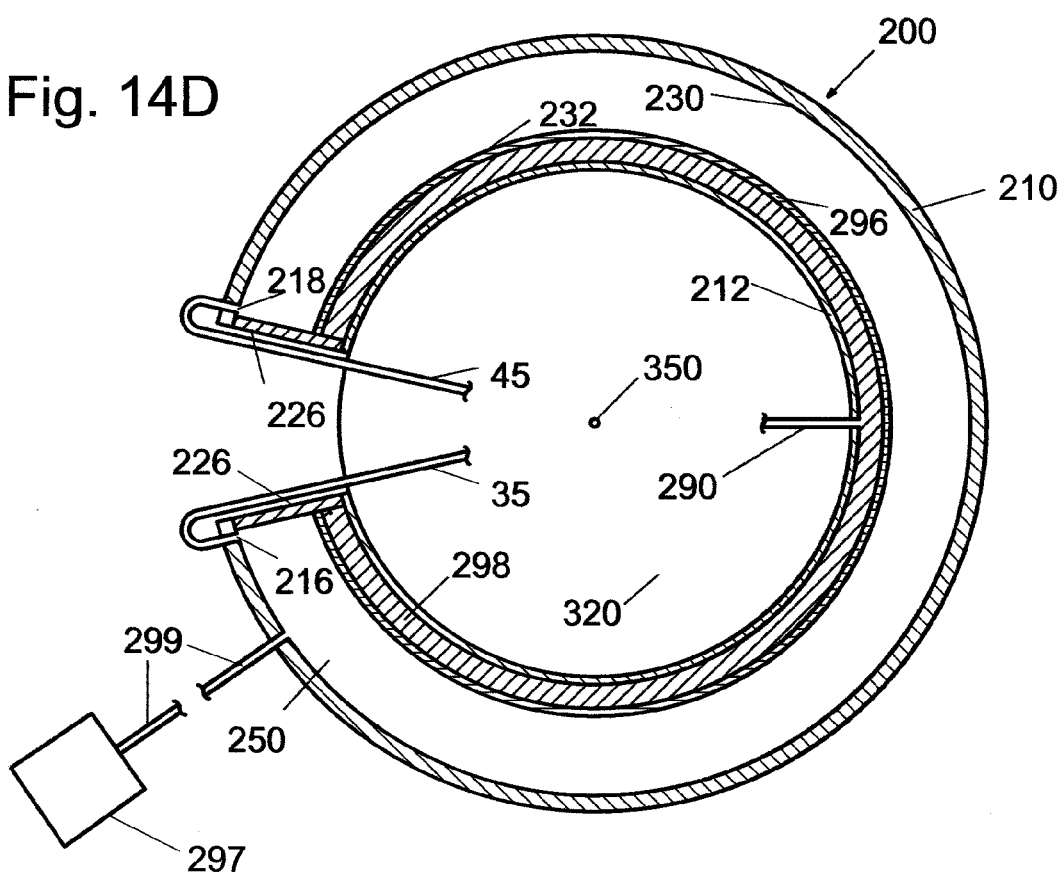
FIG. 14D, as in FIG. 6, shows a schematic cross-sectional view of the SdFFF channel assembly from a perspective that is perpendicular to fluid medium flow through a SdFFF channel and parallel to the axis of rotation. The embodiment shown in FIG. 14D incorporates components that enable the SdFFF technique to couple with asymmetrical flow field-flow fractionation (AFFFF or AF4).
Figure 14E:
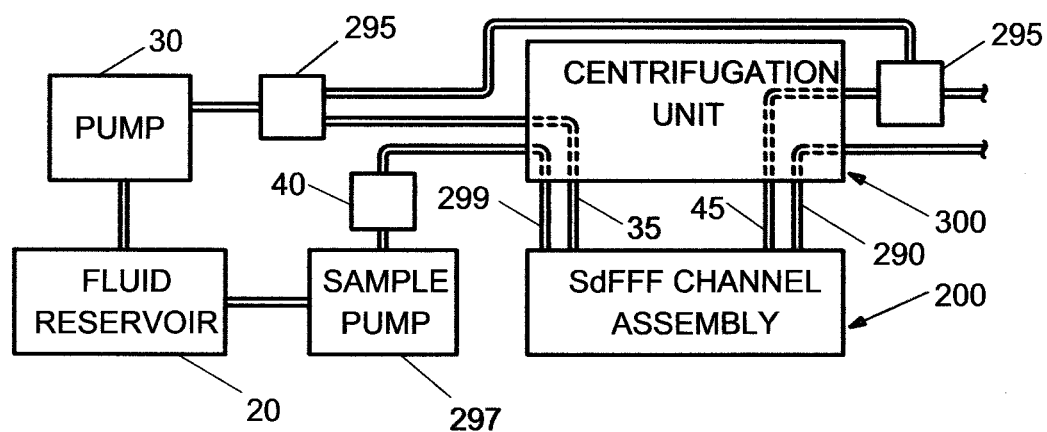
FIG. 14E shows a simplified schematic representation of one embodiment of a sedimentation field-flow fractionation (SdFFF) system that also enables asymmetrical flow field-flow fractionation (AFFFF or AF4).

FIGS. 14C, 14D, and 14E show an asymmetric variation of the FlFFF embodiment described in FIGS. 14A and 14B. Instead of using two support frits 298 and membranes 296, this variation only uses one of each. In FIG. 14C, the SdFFF channel assembly 200 and channel 250 are shown in more detail from the same perspective as in FIG. 14A. FIG. 14D shows the SdFFF channel assembly 200 from a viewpoint that is perpendicular to fluid medium flow through the SdFFF channel 250 and parallel to the axis 350 of rotation as in FIG. 6. FIG. 14E provides an overview of the entire system. All the components in FIGS. 14C and 14D are the same as in FIG. 14A, except as noted below.

The principal difference between the symmetrical and asymmetric FlFFF is the way the displacement fluid 288 is introduced into the SdFFF channel 250 to create the hydrodynamic force 272. In symmetrical FlFFF, as described above, the displacement fluid 288 is distinctly different from the fluid medium. The displacement fluid 288 flows across the channel from the membrane 296 that forms the top interior surface 230 to the membrane 296 that forms the bottom interior surface 232.

In asymmetric FlFFF, on the other hand, the displacement fluid 288 is introduced by diverting part of the fluid through the bottom interior surface 232. Only one support frit 298 and membrane 296 are required. The diverted fluid exits the SdFFF channel assembly 200 through a displacement fluid outlet 290. This change, however, generally also necessitates a change in the way the sample is introduced. In symmetrical FlFFF, the sample particles 240 enter the channel 250 through the inlet tube 35. In asymmetrical FlFFF, the sample is introduced through a separate sample inlet 299 located a short distance (typically 2-3 cm) downstream from the inlet port 216 and tube 35 as shown in FIG. 14D.

FIG. 14E shows a more general overview of one embodiment of an asymmetric FlFFF system coupled with the SdFFF. Two pumps are used: pump 30 to provide the fluid medium and a sample pump 297 to introduce the sample particles 240. Displacement fluid outlet 290 provides a path for fluid within support frit 298 (FIGS. 14C and 14D) to exit the SdFFF channel assembly 200.

In operation, fluid medium is first passed into the channel 250 through both the inlet 35 and outlet 45 tubes using controller valve 295 in such a way that the two flow streams of fluid medium meet and exit the channel 250 through the membrane 296 and support frit 298 directly opposite the sample inlet 299. With the fluid medium still flowing, the sample is then introduced using injection device 40 and pumped using sample pump 297 through the sample inlet 299 and deposited or focused against the membrane 296. Once the sample is in place, sample pump 297 is stopped and the flow of the fluid medium is redirected and allowed to move in its normal laminar flow fashion between the inlet tube 35 and the outlet tube 45. By controlling the flow through the outlet tube 45, a portion of the fluid medium is diverted through the membrane 296 and support frit 298 producing the displacement fluid 288 that creates the hydrodynamic force 272 used in the FIFFF technique.

FIG. 15A shows an embodiment of a SdFFF channel 250 that employs a plurality of outlet ports 218. While this embodiment includes only two outlet ports 218, any number of outlet ports 218 may be employed. For example, 2 to 10 outlet ports 218 may be utilized on a single SdFFF channel 250. The plurality of outlet ports 218 enable sample particles 240 (see FIG. 3) to be selectively isolated from different parts of the fluid medium as the particles 240 approach the end of the SdFFF channel 250 during the separation procedure. As an illustration, the outlet ports 218 are shown in FIG. 15A side-by-side across the width and end of the SdFFF channel 250. It should be understood that the outlet ports 218 may be positioned at predetermined locations on any part of the channel 250 in any configuration or pattern. The periphery of the outlet ports 218 may be designed to extend to predetermined positions in the channel 250 to facilitate the removal of specific fractions of particles 240 for collection from the overall sample.

The use of multiple outlet ports 218 is particularly advantageous when two-dimensional field-flow fractionation is performed. To enable this two-dimensional approach, the secondary force 260 described in FIGS. 9-14 is placed perpendicular to the sedimentation force 262 in the SdFFF channel 250 as illustrated in the embodiments shown in FIGS. 15A and 15B. Both forces 260 and 262 are also perpendicular to the direction of flow 252 of fluid medium through the channel 250. As sample particles 240 migrate through channel 250, the particles interact with the applied forces and segregate into smaller aggregates in a two-dimensional array across the width and thickness of the channel 250. The location of a particular particle within this array depends on the particle's properties and the strength of its interaction with the respective forces. For example, the sedimentation force separates particles based on differences in density. An orthogonally placed electrophoretic force would enable particles with comparable densities to be further separated in a second direction based on their electrophoretic mobility. By judiciously positioning the outlet ports 218 in the channel 250, particles with particular properties can be easily isolated. Separation resolution is greatly enhanced by adding the second dimension.

During typical operation of the embodiments shown is FIGS. 15A and 15B, fluid medium enters the SdFFF channel 250 though inlet port 216, travels the length of the channel 250 and then exits through outlet ports 218. To minimize mixing in the SdFFF channel 250 due to the Coriolis Effect, the direction of rotation 254 for the channel 250 around axis 350 is generally opposite the direction of flow 252 for the fluid medium. Sample particles 240 in the fluid medium interact with sedimentation force 262 and secondary force 260. The only difference between FIGS. 15A and 15B is the orientation of the channel 250 and forces 260 and 262.

In FIG. 15A, the sedimentation force 262 is directed across the thickness 224 of the channel and the secondary force 260 is directed across the width 222. In FIG. 15B, the orientation of the channel 250 on the rotor 320 is changed and the dimensional components of the channel 250 across which forces 260 and 262 are directed are switched. As in the description of FIG. 9, the secondary force 260 may be any force that interacts with the sample particles 240 and causes the particles 240 to move in a direction that is perpendicular to the flow of fluid medium through the SdFFF channel 250. In some modes, the secondary force 260 is developed by imposing a thermal or concentration gradient across the channel or by introducing a second independent flow stream to hydrodynamically influence the position of the particles 240. The secondary force 260 may be applied simultaneously with the sedimentation force 262 or sequentially. The individual forces 260 and 262 can be applied continuously, intermittently, or programmed to change with time during the separation procedure.

Additional flexibility is incorporated into some embodiments by including a plurality of inlet ports 216. For example, under normal operating conditions using a single inlet port 216 as shown in FIG. 15A, the fluid medium acquires a substantially parabolic velocity profile 242 (see FIG. 3) across the thickness 224 of the channel 250 as a result of the laminar flow of the fluid through the narrow channel 250. By using a second inlet port (not shown) on the other side of the channel 250 in FIG. 15A, a second stream of fluid medium can be simultaneously introduced into the channel at a different linear velocity than the first. A velocity profile can be created that is dramatically different from the original parabolic shape. By experimenting with the relative flow rates of the fluid mediums from the two inlet ports 216, or by adding additional inlet ports 216 and associated streams of fluid medium, velocity profiles can be fine-tuned to enhance separation resolution and the ability to isolate specific fractions from complex sample mixtures. As with the outlet ports 218 described above, the additional inlet ports 216 may be positioned at predetermined locations on any part of the channel 250 in any configuration or pattern.

Figure 16A:
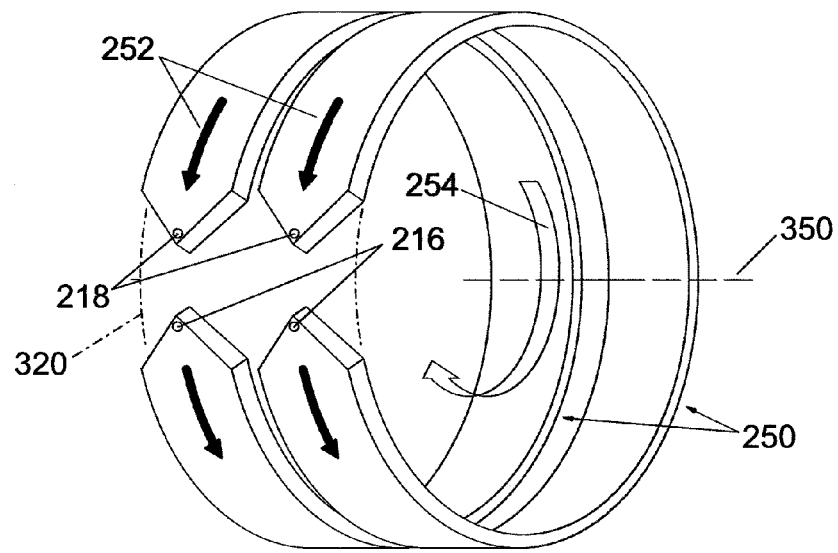
FIG. 16A shows one embodiment of multiple independent SdFFF channels configured side-by-side.

In other embodiments of the SdFFF apparatus 100, a plurality of SdFFF channels 250 can be used to greatly expand the capabilities of the apparatus. FIG. 16A shows one embodiment that incorporates two channels 250 configured side-by-side in conjunction with a single rotor 320. Operated independently in a parallel fashion, the two SdFFF channels 250 are capable of simultaneously processing multiple portions of a single sample or multiple different samples. The channels 250 may also be configured on separate rotors 320 rotating around the same axis 350. While this embodiment includes only two parallel channels 250, any number of channels 250 may be used together.

For example, 2 to 100 channels 250 may be utilized in a single SdFFF apparatus 100. As noted for FIG. 2, the SdFFF channel 250 is actually the hollow cavity through which the fluid medium flows and only has shape as provided by the SdFFF channel assembly 200 which is described in more detail in FIGS. 4-6. Each parallel channel 250 may have its own SdFFF channel assembly 200 or multiple parallel channels 250 may be incorporated into a single SdFFF channel assembly 200. During typical operation, fluid medium enters the inlet port 216, travels the length of the SdFFF channel 250, and then exits through outlet tube 218. The direction of rotation 254 for the channel 250 around axis 350 is generally opposite the direction of flow 252 for the fluid medium. The fluid medium flowing through the parallel channels 250 may be the same or different.

Figure 16B:
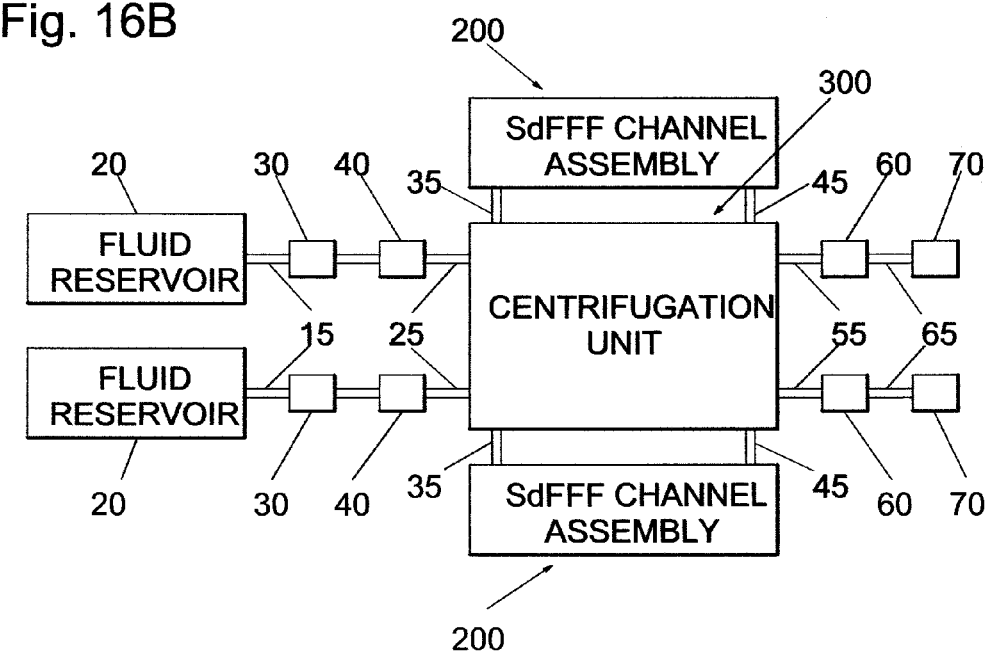
FIG. 16B shows a simplified schematic representation of one embodiment of multiple independent parallel SdFFF channel assemblies integrated into a SdFFF system.

FIG. 16B shows how the SdFFF channel assemblies 200 housing the two parallel channels 250 in FIG. 16A are integrated into the entire SdFFF system. The fluid medium flows from individual fluid reservoirs 20 through fluid communication lines 15 to pumps 30 where it is pumped through injection devices 40 using fluid communication lines 25 to the centrifugation unit 300. The same materials and devices may be used here as were discussed earlier in connection with a similar diagram in FIG. 1. When the same fluid medium is used with more than one channel 250, only a single fluid reservoir 20 and pump 30 may be necessary. The pump 30, however, generally includes a controller that enables the flow of fluid medium to the individual channels to be independently regulated. From the centrifugation unit 300, the fluid mediums flow through separate inlet tubes 35 to the respective SdFFF channel assemblies 200 and then back to the centrifugation unit 300 through separate outlet tubes 45. The connections of inlet and outlet tubes 35 and 45 to the channel 250 are made at the respective inlet and outlet ports 216 and 218 (see FIG. 16A). Each channel 250 is generally then connected to an individual detector 60 through fluid communication line 55 and to a fraction collection device 70, if required, through fluid communication line 65.

Figure 17A:
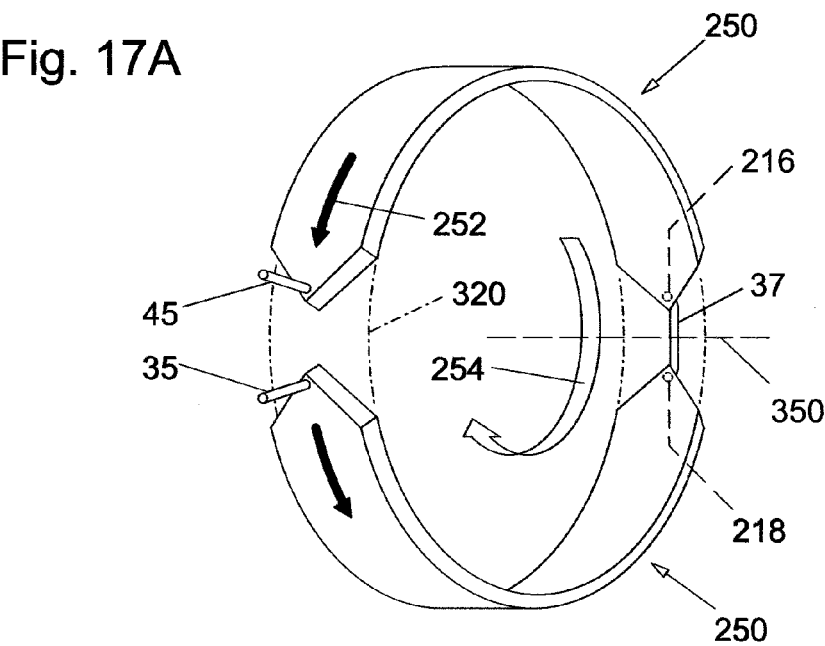
FIG. 17A shows one embodiment of multiple independent SdFFF channels configured as a unit in series.

FIG. 17A shows one embodiment of multiple independent SdFFF channels 250 configured in series capable of sequentially processing a sample. Two channels 250 are shown configured one after the other in conjunction with a single rotor 320. The two channels 250 may also be configured side-by-side in conjunction with a single rotor 320 as in FIG. 16A or on separate rotors 320 rotating around the same axis 350. Although FIG. 17A shows only two channels 250, understand that any number (2 to 10, for example) of channels 250 may be connected together in series. An outlet port 218 of each channel 250 is connected to the inlet port 216 of the subsequent channel 250 with a connecting tube 37. The fluid medium flows through the inlet tube 35 on the first channel 250 in the series and exits through the outlet tube 45 on the last channel 250 in the series. The direction of rotation 254 for the channels 250 around axis 350 is generally opposite the direction of flow 252 for the fluid medium.

Figure 17B:
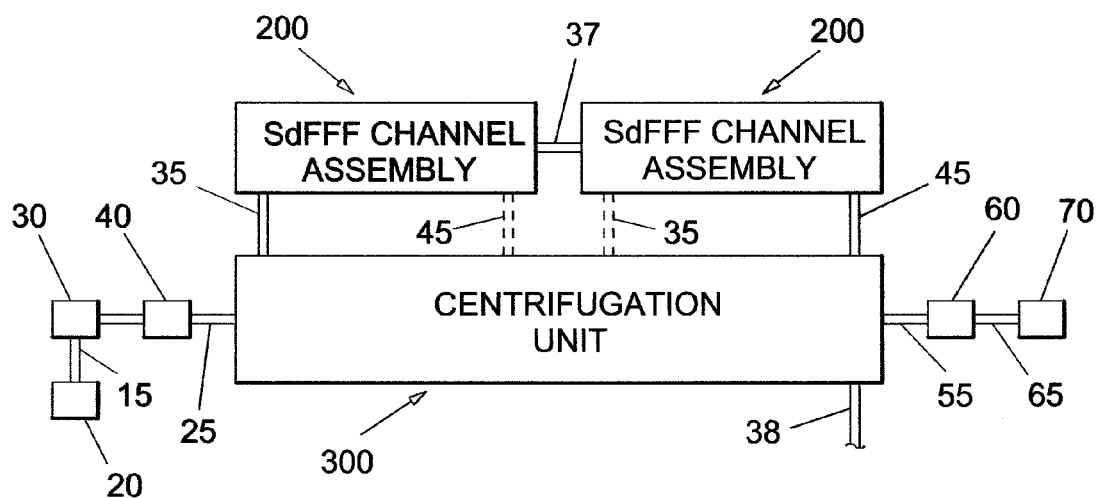
FIG. 17B shows a simplified schematic representation of one embodiment of multiple independent series SdFFF channel assemblies integrated into a SdFFF system.

In FIG. 17B, the SdFFF channel assemblies 200 housing the two series channels 250 in FIG. 17A are shown integrated into an entire SdFFF system. Since only one stream of fluid medium is necessary, the fluid flows from the fluid reservoir 20 through fluid communication line 15 to pump 30 from where the fluid is impelled by way of fluid communication line 25 through the injection device 40 to the centrifugation unit 300. From the centrifugation unit 300, the fluid medium enters the first SdFFF channel assembly 200 and channel 250 through inlet tube 35. A low volume connecting tube 37 (typically 0.02 inch ID PEEK or comparably inert tubing) then connects the first channel assembly 200 and channel 250 to the second. Outlet tube 45 returns the fluid to the centrifugation unit 300. When more than two channels 250 are connected in series, each is coupled with the subsequent channel using a connecting tube 37. Outlet tube 45 returns the fluid to the centrifugation unit 300 from the last channel 250 in the series. The fluid medium finally passes into the detector 60 and fraction collection device 70 through fluid connection tubes 55 and 65, respectively. The same materials and devices may be used here as were discussed earlier in connection with a similar diagram in FIG. 1.

It may be advantageous to use a detector in conjunction with connecting tube 37 between each channel 250 in the series to monitor movement of sample particles 240 as they travel through the progression. The intermediate detectors 60 or at least the flow cells associated with the detectors 60 are preferably mounted directly on the rotor 320. Electrical communication devices 276 to provide power and/or electrical signals to and from the detector 60 can travel through the centrifugation unit 300 using the umbilical conduit 360 described earlier in connection with FIGS. 7 and 8A. If the detector 60 is spectroscopic in nature, fiber optic cables can be run through the same umbilical conduit 360.

When operating multiple channels 250 in series, it may also be advantageous to employ a plurality of outlet ports 218 on each channel 250 to divide the fluid medium and sample particles 240 as they approach the outlet end of the channel 250 as shown in FIGS. 15A and 15B. An unwanted portion of the fluid and sample can be discarded through one outlet port 218 and tube 45 (FIG. 17B, dashed line) while a second portion continues through another outlet port 218 and a connection tube 37 to a subsequent channel 250 for further processing. The discarded portion is eliminated from the apparatus through the centrifugation unit 300 and waste tube 38.

In other embodiments, the divided fluid medium and sample can be apportioned through multiple outlet ports 218 and connection tubes 37 to multiple subsequent channels 250. The subsequent channels 250 would be parallel to each other, but in series with the first channel 250. This technique is particularly useful when two-dimensional SdFFF is used as described above in connection with FIGS. 15A and 15B. To accommodate this technique, each subsequent channel 250 generally requires at least one additional inlet port 216 to enable additional fluid medium to be introduced to adjust or maintain proper laminar flow. Each of the subsequent channels 250 can use a unique set of experimental conditions to further process the sample particles 240. The dimensions of the channels 250 and/or the flow rate of the fluid medium can be different. A secondary force 260 can be used in one channel 250 and not in the other, or two different secondary forces 260 can be used. The composition of the fluid medium can even be changed. When consideration is taken of the tremendous array of parallel and series configurations that can be integrated together and the large number of secondary forces and variations in experimental conditions that can be employed, one realizes the true potential of this invention to solve separation problems.

Figure 18:
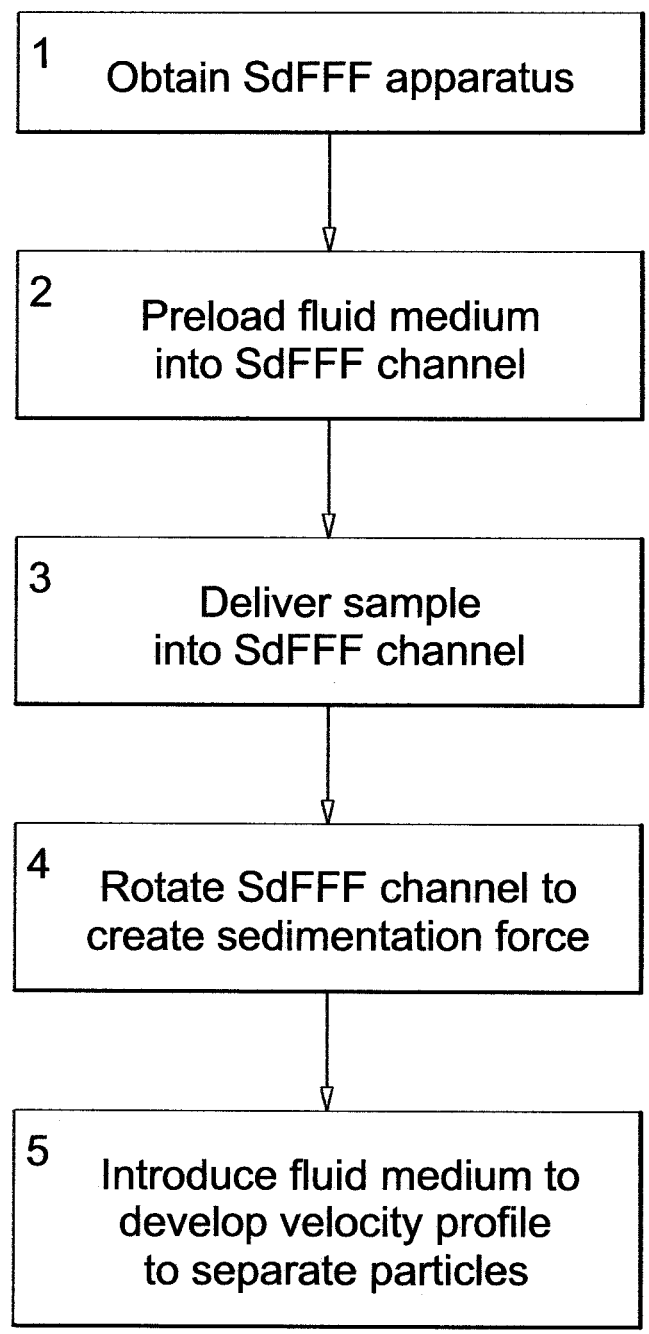
FIG. 18 shows a flowchart of a typical method for discriminating particles using the present sedimentation field-flow fractionation apparatus.

The following is a method that may be used to discriminate particles using the sedimentary field-flow fractionation (SdFFF) apparatus described above as the present invention. Any of the many embodiments may be used. As shown in a flowchart in FIG. 18, the method is comprised of five steps. (1) Obtain a SdFFF apparatus described as the present invention. (2) Preload fluid medium into the SdFFF channel of the apparatus via its inlet port until the channel is filled with fluid medium. (3) Deliver a sample that contains particles to be discriminated into the fluid medium in the channel. (4) Rotate the channel at a predetermined angular velocity about an axis to create a sedimentation force across the thickness of channel. The sedimentation force is such that it discriminates the particles in the sample by displacing the particles to various positions in the fluid medium across the thickness of channel based on the strength of an interaction between the sedimentation force and the individual particles. (5) Introduce additional fluid medium at a predetermined flow rate into the channel via its inlet port in such a way that the fluid medium travels through the channel in a laminar flow fashion and causes a velocity profile to develop across the thickness of the channel. Since the sample particles that were discriminated by the sedimentation force are located at different positions across the velocity profile, the fluid medium carries the particles to the outlet port of the channel at different velocities and thus results in a separation of the sample.

Figure 19:
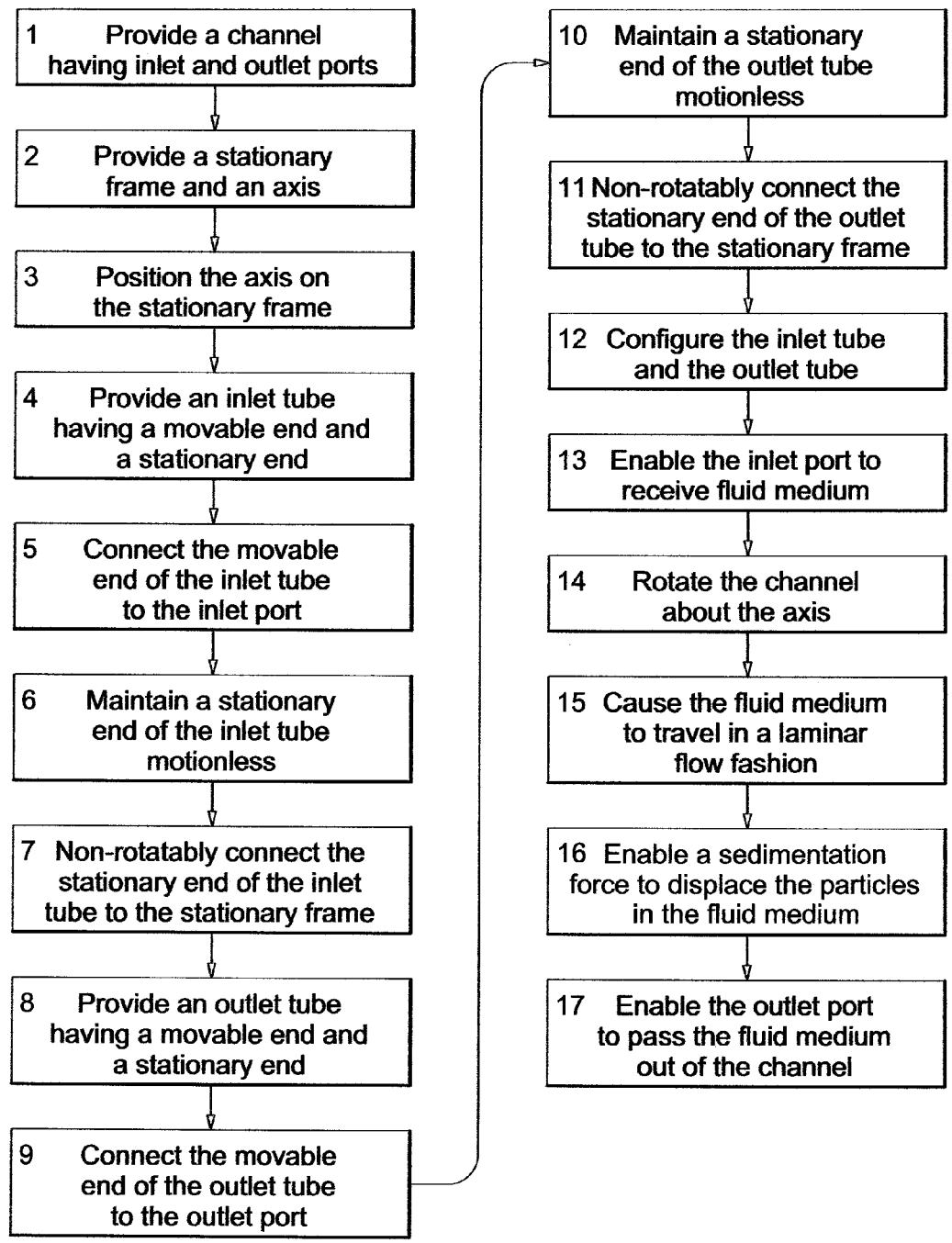
FIG. 19 is a flowchart showing the steps of a non-limiting exemplary method for discriminating particles using the present sedimentation field-flow fractionation apparatus.

Another method for discriminating particles in a fluid medium using sedimentation field-flow fractionation is shown in a flowchart in FIG. 19. This method is preferably comprised of the following steps. (1) Provide a channel having inlet and outlet ports. A width of the channel is substantially greater than a thickness thereof. (2) Provide a stationary frame and an axis. (3) Position the axis at a predetermined location on the stationary frame. (4) Provide an inlet tube having a movable end and a stationary end. (5) Connect the movable end of the inlet tube to the inlet port such that the movable end is rotatable about the axis coincidently with the channel. (6) Maintain a stationary end of the inlet tube motionless. (7) Non-rotatably connect the stationary end of the inlet tube to the stationary frame. (8) Provide an outlet tube having a movable end and a stationary end. (9) Connect the movable end of the outlet tube to the outlet port such that the movable end is rotatable about the axis coincidently with the channel. (10) Maintain the stationary end of the outlet tube motionless. (11) Non-rotatably connect the stationary end of the outlet tube to the stationary frame. (12) Configure the inlet tube and the outlet tube to allow fluid communication between the movable and stationary ends of the inlet tube and between the movable and stationary ends of the outlet tube. (13) Enable the inlet port to receive the fluid medium into the channel. (14) Rotate the channel about the axis at a predetermined angular velocity thereby creating a sedimentation force across a thickness of the channel normal to a direction of flow of the fluid medium through the channel. (15) Cause the fluid medium traveling through the channel to travel in a laminar flow fashion at different velocities according to a velocity profile across the thickness of the channel. (16) Enable the sedimentation force to displace the particles in the fluid medium to various positions across the velocity profile based on the strength of an interaction between the sedimentation force and the particles. (17) Enable the outlet port to pass the fluid medium out of the channel.

The steps in the above methods may be expanded, combined, and/or their order changed to accommodate the requirements of the specific sample, application, and/or embodiment of the SdFFF apparatus employed. Greater detail and alternative versions of the methods are given below. The methods should be familiar to one skilled in the general art of field-flow fractionation.

Under normal operating conditions, the SdFFF channel is prefilled with fluid medium by pumping fluid medium, as described for FIG. 1, from a fluid reservoir 20, through an injection device 40, and into the SdFFF apparatus 100 where the channel is located. The fluid medium should be free of dissolved gases to prevent the formation of bubbles in the channel due to outgassing. Once the channel is filled, the sampling device 40 is used to insert the sample particles into the channel as fluid medium continues to flow at an appropriate flow rate. The channel is then rotated to apply the appropriate sedimentation force. Alternatively, the order may be switched; the sedimentation force may be initiated before the introduction of the sample. Sample volumes and concentrations for analytical scale work are small, generally varying in the range of 1-50 microliters at concentrations of 0.1-2 mg/mL. The use of larger samples is discussed below.

Once the sample has been introduced into the channel, two options become available for the method. The first option is to stop the flow of the fluid medium through the channel to provide time for particle "relaxation". When the sample first enters the channel, the particles are dispersed fairly evenly across the cross-section of the channel. By halting the flow, the particles are allowed to aggregate into steady-state equilibrium zones under the influence of the applied sedimentation force without migrating significantly along the length of the channel. Relaxation times vary depending on the fluid medium and the nature of the sample, but are typically in the range from 30 seconds to 15 minutes. Optimal times are generally determined experimentally. Following the relaxation process, fluid flow is reestablished and the equilibrium zones travel through the channel to the outlet port at different velocities depending on the position of the zone in the velocity profile of the fluid medium. As the individual zones, separated in time, exit through a single channel outlet port, they generally are directed to a detector to be monitored or characterized and then, if desired, the individual zones can be collected one-by-one.

The second option after introducing the sample into the channel is to continue the flow of the fluid medium. With this option, the particles continue to travel through the channel while the steady-state equilibrium zones are formed under the influence of the applied sedimentation force. Although the second option is less time consuming than the first, it sometimes can result in spreading of the equilibrium zones and loss of separation resolution. Caution, though, must also be used with the first option.

For some samples, hydrodynamic lift forces created by the flow of the fluid medium through the channel provide a significant component to the overall forces that establish the position of the equilibrium zones in the channel. Without the flow, the zone positions are altered. In addition, sample adsorption on channel surfaces and drift in detector 60 (FIG. 1) signals can also be a problem. Careful design of the SdFFF channel, however, can sometimes mitigate the need for the stop-flow procedure. For example, with the inlet tube 35 and outlet tube 45 connected to the more radially distant side of the SdFFF channel assembly 200 as shown in FIGS. 6 and 7, sample particles enter the channel closer to the ultimate locations of the steady-state equilibrium zones than had the tubes been connected to the less radially distant side of the channel assembly.

In utilizing the method, the sedimentation force may be applied continuously to the particles in the channel at a fixed strength or intermittently by starting and stopping the rotation of the channel around the axis. In addition, the sedimentation force may be programmed or changed systematically. For a channel at a fixed radial distance from the axis, the strength of the sedimentation force is related to the square of the rotational velocity of the channel about the axis.

Sample resolution can also be a function of the size of the sample. In fact, the use of large sample volumes can necessitate the change from a channel with a single outlet port to one with multiple outlet ports across the thickness of the channel. The steady state equilibrium zones that form in the channel are three-dimensional in nature with a breadth (across the thickness of the channel), a width (across the width of the channel) and a span (along the length of the channel). Increasing the volume of the sample generally also increases the span of each zone. The breadth is restricted by the balancing of opposing equilibrium forces. Ultimately, if the sample becomes large enough, the zones stretch from the inlet port of the channel to the outlet port. There is no differentiation of the zones along the length of the channel. Resolution of the zones is then only possible across the thickness direction of the channel. To isolate the individual zones, a different outlet (and detector) must be provided for each zone. Five zones, for example, would require five outlets. The method must be modified to reflect the fact that the zones are collected simultaneously rather than one at a time.

FIGS. 9-14E show embodiments of the SdFFF channel assembly 200 that incorporate components that enable the generation of a secondary force across the thickness 224 of the SdFFF channel 250. These embodiments facilitate the coupling of the SdFFF technique with other modes of field-flow fractionation (FFF) such as electrical FFF (EFFF), dielectrophoretic FFF (DEP-FFF), magnetic FFF (MgFFF), thermal FFF (ThFFF), flow FFF (FlFFF), and asymmetric flow FFF (AFFFF or AF4). Understand that the present invention is not limited to just these examples. The secondary force may be any force that interacts with the sample particles and causes the particles to move in a direction that is perpendicular to the flow of fluid medium through the SdFFF channel 250. These were chosen to highlight how the present invention makes possible the coupling of a wide range of field-flow fractionation technologies requiring only simple modifications to the SdFFF channel assembly.

Non-Limiting Exemplary Methods

The methods used with these embodiments are the same, with few exceptions, as those described above. Typically the secondary force 260 is introduced in such a way that it opposes the sedimentation force 262 created by the rotation of SdFFF channel 250 around axis 350. In other methods, however, it may be advantageous for the secondary force 260 and sedimentation force 262 to be aligned in the same direction. The secondary force 260 may be applied simultaneously with the sedimentation force 262 or sequentially. Either or both forces may be applied, continuously, intermittently, or changing in strength with time. More explicit method details concerning the application of specific secondary forces and their generation are provided above in connection with the descriptions of FIGS. 10-14E.

Particle relaxation procedures can be modified when a secondary force mechanism has been incorporated into the SdFFF channel assembly 200. Instead of stopping the flow of the fluid medium as described above, the secondary force can be used to rapidly drive the particles into the slower moving flow streams near the channel surface closest to where the equilibrium zones should finally occur. Once there, the secondary force is turned off or diminished and normal field-flow fractionation is allowed to proceed. Carried to an extreme, this method can also be used to hold and concentrate dilute samples. Instead of just slowing the sample particles, enough force is applied to seize the particles against the surface of the channel immediately past the inlet port. Additional portions of sample are then added and held until the total quantity of sample in the channel is deemed adequate. Assuming no irreversible adsorption has occurred, the sample is then released in mass by turning off or diminishing the secondary force. The procedure can also be used to selectively restrain a particular component of a sample mixture. For example, an electrophoretic force can be employed to hold only charged particles, easily separating them from electrically neutral particles in the sample.

In other embodiments of the SdFFF apparatus 100, a plurality of SdFFF channels 250 are used to greatly expand the capabilities of the apparatus. FIG. 16A shows one embodiment that incorporates two channels 250 configured side-by-side in conjunction with a single rotor 320. When operated independently in a parallel fashion, the method is the same as outlined above. As shown in FIG. 16B, each SdFFF channel has its own pump 30, injection device 40, and detector 60. The two SdFFF channels 250 are capable of simultaneously processing different samples (a standard and an unknown for example) or multiple portions of a single sample. The fluid medium flowing through the parallel channels 250 may be the same or different.

FIGS. 17A and 17B show an embodiment of two SdFFF channels 250 configured in series capable of sequentially, but independently, processing a sample. As with the above methods, fluid medium is pumped from a fluid reservoir 20, through an injection device 40, and into the SdFFF channel assembly 200 where the channel is located. In this embodiment, the fluid medium then continues into a second channel assembly 200 housing the second channel 250 and then to the detector 60 and fraction collection device 70.

As just described, any sample introduced through the injection device ultimately passes through both channels. In some embodiments, a plurality of outlet ports are employed on the each channel 250 to subdivide the fluid medium and sample as they approach the outlet end of the channel 250. An unwanted portion of fluid and/or sample can be discarded through one outlet port while a second portion continues through another outlet port and to a subsequent channel 250 for further processing.

In other embodiments, the divided fluid medium and sample can be apportioned through multiple outlet ports and directed to multiple subsequent channels 250. The subsequent channels 250 could be parallel to each other, in series, or a combination thereof. This technique is particularly useful when two-dimensional SdFFF is used as described above in connection with FIGS. 15A and 15B or where large samples are used that need further processing. To accommodate this technique, each subsequent channel 250 generally requires at least one additional inlet port to enable additional fluid medium to be introduced to adjust or maintain proper laminar flow. Each subsequent channel 250 can use a unique set of experimental conditions to process the sample particles.

Advantages and Ramifications

Sedimentation field-flow fractionation is a single-phase elution-based particle separation and characterization technique. What makes the current invention unique is that it provides a simple and expandable apparatus and method that enable sedimentation field-flow fractionation separations to be performed without the use of rotating seals to transport fluids in and out of the rotating separation channel. To eliminate the seals, this invention couples the rotating field-flow fractionation channel to a looping-tube twist-compensating continuous-flow centrifugation system as described above. Despite the fact that both sedimentation field-flow fractionation [J. C. Giddings, F. J. F. Yang, M. N. Myers, "Sedimentation Field-Flow Fractionation", Anal. Chem., 46 1917-1924 (1974)] and the centrifugation system [Baxter Laboratories (1976), U.S. Pat. No. 3,986,442] were first introduced in the 1970's, the two techniques have never been employed together. Even sedimentation field-flow fractionation systems described and patented as recently as October 2008 [Philippe Cardot, Université de Limoges (2008), U.S. Pat. No. 7,442,315] still use rotating seals to provide fluid communication with the rotating separation channel. By eliminating the need for these seals, the present invention significantly improves the resolution of sedimentation field-flow fractionation separations, decreases maintenance, and enables the use of equipment and methodologies that have the potential to dramatically broaden the applicability of the technique to a more diverse array of samples in biology, chemistry, environmental and marine sciences, medicine, and nanotechnology.

The advantages of the present invention are significant.

1. The apparatus and method eliminate the leakage, contamination risks, and frequent maintenance problems often encountered with sedimentation field-flow fractionation systems that employ rotating seals to provide fluid communication with the rotating channel. The absence of these seals also permits the use of higher fluid flow rates and narrower internal diameter tubing which helps decrease analysis times and minimizes extra-channel band spreading of separated sample particles.

2. The apparatus and method enable the use of multiple continuous, non-broken connections to the rotating separation channel from peripheral devices associated with the system using conventional construction materials such as tubing, wires, or fiber optics. These connections can be for any purpose and type including, but not limited to, the transport of fluids, samples, signals, and/or mechanical actions.

3. The apparatus and method enable the use of one or more secondary forces in addition to sedimentation to bring about the field-flow fractionation discrimination and separation of sample particles. The secondary force can be any force that is able to interact with the sample particles and cause the particles to move. The degree of displacement is based on the strength of the interaction between the force and particles, and the magnitude of opposing forces. The use of two or more simultaneous forces has the potential to greatly enhance the selectivity in the separation by providing additional parameters that can be manipulated to differentiate the properties of the sample particles.

4. Using secondary forces, the apparatus and method permit greater flexibility in the particle relaxation procedure and provide a technique to concentrate sample particles near the inlet port of the separation channel. This minimizes the initial width (volume) of the sample in the channel and makes possible a final sample separation exhibiting greater resolution at higher particle concentrations. Depending on the secondary force employed, this same procedure can also be used to selectively isolate particles with a particular characteristic (all magnetically susceptible particles, for example).

5. The apparatus is designed to enable simple installation and adjustment of the separation channel. Without rotating seals on both sides of the rotor, access is unencumbered. Rotors are easily exchanged with the channel preinstalled or the channel can be installed with the rotor already mounted on the apparatus. The channel can be prefabricated or constructed piece-by-piece on the rotor.

6. The apparatus is designed to enable the sample injection device and/or the detector to be mounted directly on the rotor. This configuration minimizes band spreading of the sample particles by eliminating the need for lengthy connective tubing directly before or after the separation channel. The apparatus can accommodate either manual or automatic activation of the injection device using many different types of activation methods (electrical, mechanical, or hydraulic).

7. The apparatus and method are designed to permit the simultaneous use of two or more separation channels connected to a single sample introduction system or multiple (individual) sample introduction systems. Depending on the size (circumference and width) of the rotor, the channels can be side-by-side, end-to-end, or stacked. Channels can be operated independently, each with a different set of experimental conditions, or in concert. Such a system can be used to increase both the resolution of sample components and the total sample throughput. Using configurations that incorporate both parallel and serial connections, the apparatus and method described in this invention make possible a wide array of particle separations that are not possible with sedimentary field-flow fractionation systems that employ rotating seals.

While an exemplary embodiment of the invention has been described, it should be apparent that modifications and variations thereto are possible, all of which fall within the true spirit and scope of the invention. With respect to the above description then, it is to be realized that the optimum relationships for the components, including variations in order, form, content, function and manner of operation, are deemed readily apparent and obvious to one skilled in the art, and all equivalent relationships to those illustrated in the drawings and described in the specification are intended to be encompassed by the present invention.

The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

What is claimed as new and what is desired to secure by Letters Patent of the United States is:

1. An apparatus for sedimentation field-flow fractionation for the discrimination of particles in a fluid medium, comprising:

a channel having an inlet port adapted to receive said fluid medium into said channel, said channel further having an outlet port adapted to pass said fluid medium out of said channel, said channel further having a width substantially greater than a thickness thereof which causes said fluid medium traveling through said channel to travel in a laminar flow fashion at different velocities according to a velocity profile across the thickness of said channel;

a stationary frame and an axis, said axis being positioned at a predetermined location on said stationary frame;

means for rotating said channel about said axis at a predetermined angular velocity thereby creating a sedimentation force across a thickness of said channel normal to a direction of flow of said fluid medium through said channel, said sedimentation force displacing said particles in said fluid medium to various positions across said velocity profile based on the strength of an interaction between said sedimentation force and said particles;

an inlet tube having a movable end and a stationary end, said movable end of said inlet tube being connected to said inlet port and further being rotatable about said axis coincidently with said channel, said stationary end of said inlet tube being motionless and non-rotatably connected to said stationary frame;

an outlet tube having a movable end and a stationary end, said movable end of said outlet tube being connected to said outlet port and further being rotatable about said axis coincidently with said channel, said stationary end of said outlet tube being motionless and non-rotatably connected to said stationary frame; and means for configuring said inlet tube and said outlet tube to allow fluid communication between said movable and stationary ends of said inlet tube and between said movable and stationary ends of said outlet tube.

2. The apparatus according to claim 1, wherein said means for rotating said channel about said axis and wherein said means for configuring said inlet and outlet tubes to allow fluid communication free of said rotating seals between said movable and stationary ends of said inlet and outlet tubes comprises a centrifugation unit, said centrifugation unit comprising:

a rotating guide frame and said stationary frame, said rotating guide frame being rotatably mounted to said stationary frame for rotation about said axis, a rotor, said rotor being rotatably mounted to said rotating guide frame for rotation about said axis; a stationary point located at a predetermined distance outside said rotor along the axis on said stationary frame;

wherein said rotating guide frame directs said inlet tube and said outlet tube into a fishhook-shaped path between their respective stationary ends and movable ends; drive means for rotating said rotor and said rotating guide frame in a same direction about said axis;

whereby said inlet tube and said outlet tube are adapted to permit fluid communication free of said rotating seals between said movable and stationary ends of said respective inlet and outlet tubes without twisting and tangling said inlet and outlet tubes during rotation of said rotor and said channel.

3. The apparatus according to claim 1, further comprising: an electrical communication device for providing electrical communication between said channel and said stationary frame.

4. The apparatus according to claim 1, further comprising: a fluid communication device for providing fluid communication between said channel and said stationary frame.

5. The apparatus according to claim 1, further comprising: a secondary force means for creating a secondary force across a thickness of said channel normal to the direction of flow of said fluid medium through said channel, said secondary force displacing said particles in the fluid medium to various positions across a velocity profile based on a strength of interaction between said secondary force and said particles; said apparatus thereby being able to use said sedimentation force and the secondary force in the discrimination of said particles in said fluid medium.

6. The apparatus according to claim 1, further comprising: a secondary force means for creating a secondary force across a width of said channel normal to a direction of flow of said fluid medium through said channel, said secondary force displacing said particles in the fluid medium to various positions across the width of said channel based on a strength of interaction between said secondary force and said particles; said apparatus thereby being able to use said sedimentation force and the secondary force in the discrimination of said particles in said fluid medium.

7. The apparatus according to claim 5, wherein said sedimentation force and said secondary force are applied simultaneously in the discrimination of said particles in said fluid medium.

8. The apparatus according to claim 5, wherein said sedimentation force and said secondary force are applied sequentially in the discrimination of said particles in said fluid medium.

9. The apparatus according to claim 5, wherein said secondary force is an electrical force and said secondary force means comprises: a plurality of electrodes, said plurality of electrodes being adapted along a portion of said channel, said plurality of electrodes being energized by an electrical signal provided by an electrical signal generator to create said electrical force across said thickness of said channel normal to the direction of flow of said fluid medium through said channel.

10. The apparatus according to claim 5, wherein said secondary force is a dielectrophoretic force and said secondary force means comprises: a plurality of electrodes, said plurality of electrodes being adapted along a portion of said channel, said plurality of electrodes being energized by an electrical signal provided by an electrical signal generator to create said dielectrophoretic force across said thickness of said channel normal to the direction of flow of said fluid medium through said channel.

11. The apparatus according to claim 5, wherein said secondary force is a magnetic force and said secondary force means comprises: a magnet, said magnet being adapted along a portion of said channel, said magnet creating said magnetic force across the thickness of said channel normal to the direction of flow of said fluid medium through said channel.

12. The apparatus according to claim 5, wherein said secondary force is a thermophoretic force and said secondary force means comprises: a top interior surface and a bottom interior surface at different temperatures, said top interior surface and said bottom interior surface creating said thermophoretic force across the thickness of said channel normal to the direction of flow of said fluid medium through said channel.

13. The apparatus according to claim 5, wherein said secondary force is a hydrodynamic force and said secondary force means comprises: a displacement fluid flowing across the thickness of said channel normal to the direction of flow of said fluid medium through said channel, said displacement fluid exerts said hydrodynamic force displacing said particles in the fluid medium to various positions across said velocity profile.

14. The apparatus according to claim 1, further comprising: an injection device, wherein said channel is adapted to be connected to said injection device for introducing said particles into said fluid medium.

15. The apparatus according to claim 14, wherein said injection device rotates congruently with said channel about said axis.

16. The apparatus according to claim 1, further comprising: a detector, wherein said channel is connected to said detector for detecting said particles in said fluid medium.

17. The apparatus according to claim 16, wherein said detector rotates congruently with said channel about said axis.

18. The apparatus according to claim 1, wherein said channel comprises: a plurality of channels, said channels rotating congruently about said axis, said channels each having corresponding ones of said inlet and outlet ports.

19. A method for discriminating particles in a fluid medium using sedimentation field-flow fractionation, said method comprising:
providing a channel having inlet and outlet ports, said channel further having a width substantially greater than a thickness thereof;
providing a stationary frame and an axis;
positioning said axis at a predetermined location on said stationary frame;
providing an inlet tube having a movable end and a stationary end;
connecting said movable end of said inlet tube to said inlet port such that said movable end is rotatable about said axis coincidently with said channel;
maintaining said stationary end of said inlet tube motionless;
non-rotatably connecting said stationary end of said inlet tube to said stationary frame;
providing an outlet tube having a movable end and a stationary end;
connecting said movable end of said outlet tube to said outlet port such that said movable end is rotatable about said axis coincidently with said channel;
maintaining said stationary end of said outlet tube motionless;

non-rotatably connecting said stationary end of said outlet tube to said stationary frame;

configuring said inlet tube and said outlet tube to allow fluid communication between said movable and stationary ends of said inlet tube and between said movable and stationary ends of said outlet tube;

said inlet port receiving said fluid medium into said channel;

rotating said channel about said axis at a predetermined angular velocity thereby creating a sedimentation force across a thickness of said channel normal to a direction of flow of said fluid medium through said channel;

causing said fluid medium traveling through said channel to travel in a laminar flow fashion at different velocities according to a velocity profile across the thickness of said channel;

said sedimentation force displacing said particles in said fluid medium to various positions across said velocity profile based on the strength of an interaction between said sedimentation force and said particles; and said outlet port passing said fluid medium out of said channel.

20. An apparatus for sedimentation field-flow fractionation for the discrimination of particles in a fluid medium, comprising:

a channel having a thickness, a width, and a length, all predetermined; said channel having two ends, two sides, a top interior surface, and a bottom interior surface; said top interior surface and said bottom interior surface being uniformly equidistant apart, said thickness being the distance between said top interior surface and said bottom interior surface; said width being the distance between said sides, said length being the distance between said ends measured on a line midway between said top interior surface and said bottom interior surface; said channel having at least one inlet port located substantially towards one end of said channel for passing said fluid medium into said channel and said channel having at least one outlet port located substantially towards the other end of said channel for passing said fluid medium out of said channel; said channel further having a substantially greater width than thickness which causes said fluid medium traveling through said channel to travel in a laminar flow fashion at different velocities according to a velocity profile across the thickness of said channel;

a stationary frame and an axis, said axis being positioned at a predetermined location on said stationary frame;

a means for rotating said channel about said axis at a predetermined angular velocity creating a sedimentation force across the thickness of said channel normal to the direction of flow of said fluid medium through said channel, said sedimentation force displacing said particles in the fluid medium to various positions across said velocity profile based on the strength of an interaction between said sedimentation force and said particles;

at least one inlet tube, said inlet tube being flexible and having a movable end and a stationary end, said movable end of said inlet tube being connected to said inlet port on said channel and said movable end being rotatable about said axis coincidently with said channel, said stationary end of said inlet tube being motionless and non-rotatably connected to said stationary frame, said inlet tube being continuous between said movable end and said stationary end;

at least one outlet tube, said outlet tube being flexible and having a movable end and a stationary end, said movable end of said outlet tube being connected to said outlet port on said channel and said movable end being rotatable about said axis coincidently with said channel, said stationary end of said outlet tube being motionless and non-rotatably connected to said stationary frame, said outlet tube being continuous between said movable end and said stationary end; and a means for configuring, in combination, said inlet tube and said outlet tube, including said movable and stationary ends of each, to allow fluid communication free of rotating seals between said movable and stationary ends of said inlet tube and between said movable and stationary ends of said outlet tube; said means for configuring preventing twisting and tangling of said inlet and outlet tubes during rotation of said channel.

* * * * *